(12) United States Patent
Knapp et al.

(10) Patent No.: US 8,215,496 B2
(45) Date of Patent: Jul. 10, 2012

(54) POLYNORBORNENE PERVAPORATION MEMBRANE FILMS, PREPARATION AND USE THEREOF

(75) Inventors: Brain Knapp, Medina, OH (US);
Edmund Elce, Lakewood, OH (US);
Brian Bedwell, Palo Alto, CA (US);
Leah J. Langsdorf, Akron, OH (US);
Ryan Wilks, Hudson, OH (US)

(73) Assignee: Promerus LLC, Brecksville, OH (US)

( * ) Notice: Subject to any disclaimer, the term of this patent is extended or adjusted under 35 U.S.C. 154(b) by 669 days.

(21) Appl. No.: 12/360,820

(22) Filed: Jan. 27, 2009

(65) Prior Publication Data

US 2009/0188863 A1 Jul. 30, 2009

Related U.S. Application Data

(60) Provisional application No. 61/024,043, filed on Jan. 28, 2008.

(51) Int. Cl.
*B01D 39/00* (2006.01)
*B01D 39/14* (2006.01)

(52) U.S. Cl. .......... 210/500.28; 210/500.23; 210/500.33

(58) Field of Classification Search ........................ None
See application file for complete search history.

(56) References Cited

U.S. PATENT DOCUMENTS

| | | | |
|---|---|---|---|
| 5,006,576 A | 4/1991 | Pasternak et al. | |
| 5,741,869 A * | 4/1998 | Goodall et al. | 526/171 |
| 6,755,975 B2 | 6/2004 | Vane et al. | |
| 2004/0248034 A1 * | 12/2004 | Henderson et al. | 430/270.1 |
| 2006/0008734 A1 | 1/2006 | Amoroso et al. | |
| 2007/0031954 A1 | 2/2007 | Mairal et al. | |

OTHER PUBLICATIONS

Smitha et al. Separation of organic-organic mixtures by pervaporation—a review. Journal of Membrane Science 241 (2004) 1-21.*
International Search Report for International Application No. PCT/US 09/32219 dated Mar. 16, 2009.
Written Opinion of the International Searching Authority for International Application No. PCT/US 09/32219 dated Mar. 16, 2009.
Wang, et al "Pervaporation separation of aqueous alcohol solution through a carbazole-functionalized norbornene derivative membrane using living ring-opening metathesis polymerization," Journal of Membrane Science 246 (2005) 59?65, Jan. 2005.
Uragami et al. "Permeation and Separation Characteristics of Alcohol-Water Mixtures through Poly(dimethyl Siloxane) Membrane by Pervaporation and Evapomeation", Journal of Applied Polymer Science, vol. 44, pp. 2009-2018 (1992).
Tadashi Uragami, "Structural Design of Polymer Membranes for Concentration of Bio-ethanol", Polymer Journal, vol. 40, No. 6, pp. 485-494, 2008.
Qureshi et al. "Fouling Studies of a Pervaporation Membrane with Commercial Fermentation Media and Fermentation Broth of Hyper-Butanol-Producing *Clostridium beijerinckii* BA101", Separation Science & Technology, vol. 34, No. 14, pp. 2803-2815, 1999.

(Continued)

*Primary Examiner* — Krishnan S Menon
*Assistant Examiner* — Katherine Zalasky
(74) *Attorney, Agent, or Firm* — Turocy & Watson, LLP

(57) ABSTRACT

Embodiments in accordance with the present invention provide forming polynorbornenes useful for forming pervaporation membranes, the membranes themselves and methods of making such membranes.

26 Claims, 14 Drawing Sheets

OTHER PUBLICATIONS

Leland M Vane, "A review of pervaporation for product recovery from biomass fermentation processes", J Chem Technol Biotechnol 80:603-629 (2005).

European Search Report for EP Application No. 09704954.8, dated Jun. 28, 2011, 11 pages.

Thrasher et al. "Transport of Water and Methanol Vapors in Alkyl Substituted Poly(norbornene)" Polymer, Elsevier Science Publishers BV, GB, vol. 45, No. 8, pp. 2641-2649 Apr. 1, 2004.

Meuleman et al. "EPDM as a Selective Membrane Material in Pervaporation" Journal of Membrane Science, vol. 188, No. 2, pp. 235-249, Jul. 15, 2001.

European Office Action for EP Application No. 09704954.8, dated Jul. 15, 2011, 1 page.

Chinese Office Action for Chinese Application No. 200980103404.0 mailed on Oct. 21, 2011.

* cited by examiner (A) (B) (C) (D) (E) (F)

(A) (B) (C) (D) (E) (F)

(A) (B) (C) (D) (E) (F)

POLYNORBORNENE PERVAPORATION MEMBRANE FILMS, PREPARATION AND USE THEREOF

CROSS-REFERENCE TO RELATED APPLICATIONS

This application claims the benefit of priority to U.S. Provisional Application Ser. No. 61/024,043 filed Jan. 28, 2008, the entire contents of which are hereby incorporated by reference.

TECHNICAL FIELD

The present invention relates generally to polynorbornenes suitable for use as pervaporation membrane films and more specifically the composition and preparation of such polymers, membrane films made from such polymers and the use of such membrane films for pervaporation processes.

DETAILED DESCRIPTION

Figure 1:
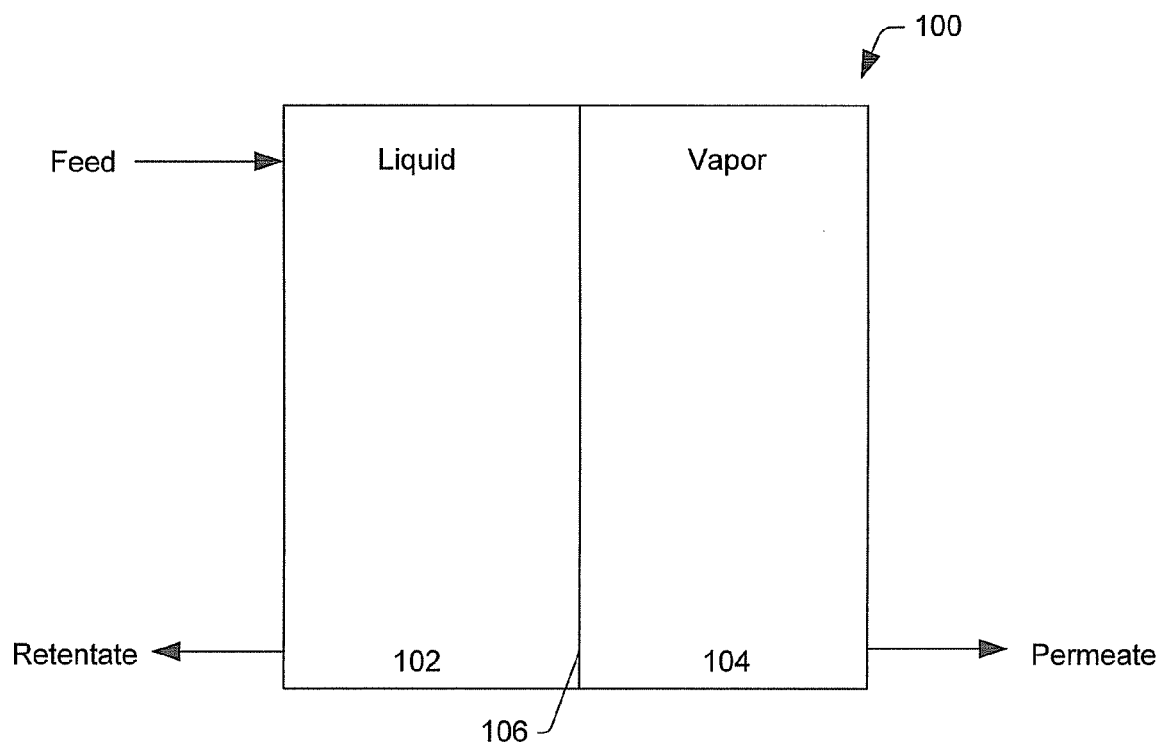
FIG. 1 depicts a pervaporation module in accordance with one aspect of the invention.

There is an ongoing need to separate organic material from water. The need for such a separation can range from the purification of a water stream accidentally contaminated by an industrial process to the isolation of an organic product from an aqueous fermentation broth used to form such a chemical material via a biological process, for example the creation of a biofuel from the broth of a fermentation reactor or any other biologically formed broth, e.g., an algae broth. While it is well known to use processes such as distillation and gas stripping to effect such separations, these conventional processes, particularly distillation, are generally characterized by high capital and energy costs thus often making such conventional processes problematic, for example, it has noted that in excess of 60% of the heating value of a biofuel such as butanol can be "wasted" if conventional separation processes are employed.

Therefore, an alternate process for effecting such separations known as pervaporation has received considerable attention as a solution to the aforementioned "waste". In a pervaporation process, a charge liquid, often a fermentation broth, is brought into contact with a membrane film having the property to allow one component of the charge liquid to preferentially permeate the membrane. This permeate is then removed as a vapor from the downstream side of the membrane film. While polymers such as polyimides, polydimethylsiloxanes and the like have been used to form pervaporation membranes with some successes, to date, none have demonstrated the necessary characteristics to become a commercial success.

Exemplary embodiments of the present invention will be described hereinbelow. Various modifications, adaptations or variations of such exemplary embodiments may become apparent to those skilled in the art as such are disclosed. It will be understood that all such modifications, adaptations or variations that rely upon the teachings of the present invention, and through which these teachings have advanced the art, are considered to be within the scope and spirit of the present invention. For example, while the exemplary embodiments described herein generally reference the separation of butanol from an aqueous charge liquid, such are not meant to limit the present invention only to embodiments for butanol separation. Thus some embodiments of the present invention encompass the separation of any organic material from an aqueous based charge liquid where an appropriate polynorbornene pervaporation membrane can be formed. For example, some embodiments encompass the separation of a hydrophobic organic material from a hydrophilic charge liquid using an appropriate polynorbornene pervaporation membrane. Still other embodiments of the present invention encompass separation of non-polar and polar organic materials. Examples of such separations include, but are not limited to, aromatics such as benzene or toluene from water miscible alcohols such as methanol or ethanol and the separation of non-polar hydrocarbyl-based materials such as hexanes and heptanes from polar heterocarbyl-based materials.

In addition, unless otherwise indicated, all numbers, values and/or expressions referring to quantities of ingredients, reaction conditions, % absorption, and the like, that are used herein are to be understood as modified in all instances by the term "about."

Further, any numerical ranges disclosed herein will be understood to be continuous, and inclusive of every value between the minimum and maximum values of each range. Unless expressly indicated otherwise, such numerical ranges are approximations that are reflective of the various uncertainties of measurement encountered in obtaining such values.

The expected behavior of a pervaporation membrane made of a hydrophobic polymer is to become plasticized and/or swollen as the organic concentration increases. Plasticized and/or swollen membranes generally cause an undesirable increase in permeability of both the organic and water, with the water permeability generally increasing relatively more than the organic permeability thus resulting in a reduction in separation factor. Plasticized and/or swollen membranes also generally cause an undesirable decrease in flux. Unexpectedly, polynorbornene pervaporation membranes, which are generally hydrophobic, exhibit a behavior opposite as to what is generally expected. Polynorbornene pervaporation membranes as described herein have a separation factor that increases dramatically with increasing feed concentration (that is, an increase in the organic concentration of a feed stream).

Typically in pervaporation, a multi-component liquid stream is passed across a pervaporation membrane that preferentially permeates one or more of the components. As the multi-component liquid stream flows across the pervaporation membrane surface, the preferentially permeated components pass through the pervaporation membrane and are removed as a permeate vapor. Transport through the pervaporation membrane is induced by maintaining a vapor pressure on the permeate side of the pervaporation membrane that is lower than the vapor pressure of the multi-component liquid stream. The vapor pressure difference can be achieved, for example, by maintaining the multi-component liquid stream at a higher temperature than that of the permeate stream. In this example, the latent heat of evaporation of the permeate components is supplied to the multi-component liquid stream for maintaining the feed temperature and for continuing the pervaporation process. Alternatively, the vapor pressure difference is typically achieved by operating at below atmospheric pressure on the permeate side of the pervaporation module. A partial vacuum on the permeate side of the polynorbornene pervaporation membrane can be obtained by any one of: relying on the pressure drop that occurs as a result of the cooling and condensation that takes place in the condenser unit, and/or by use of a vacuum pump. An optional sweep gas on the permeate side can facilitate the pervaporation process by lowering the concentration of the permeating components. The vapor pressure of the feed liquid can be optionally raised by heating the fermentation broth.

A schematic diagram of the pervaporation process is shown in FIG. 1. As depicted, a feed containing numerous species is charged into a pervaporation module 100 and to a liquid chamber 102 on the feed side thereof. Vapor chamber 104 on the permeate side is separated from the liquid chamber 102 by a pervaporation membrane 106. The vapor phase is extracted from the feed liquid through the pervaporation membrane 106 which is selective for a given permeate, and the permeate vapor, which is enriched in the given permeate relative to the feed liquid, is removed from the pervaporation module 100, generally by condensation thereof.

Utilizing polynorbornene pervaporation membranes, pervaporation can be employed to treat a fermentation broth containing, for example, biobutanol and one or more other miscible components. More specifically, a fermentation broth can be to liquid chamber 102 and thus placed in contact with one side of polynorbornene pervaporation membrane 106 while a vacuum or gas purge is applied to vapor chamber 104. The fermentation broth can be heated or unheated. The components in the fermentation broth sorb into/onto polynorbornene pervaporation membrane 106, permeate through and evaporate into the vapor phase. The resulting vapor or permeate, for example butanol, is then condensed and collected. Due to different species in the fermentation broth having different affinities for the polynorbornene pervaporation membrane and different diffusion rates through the membrane, even a component at low concentration in the feed can be highly enriched in the permeate.

Figure 2:
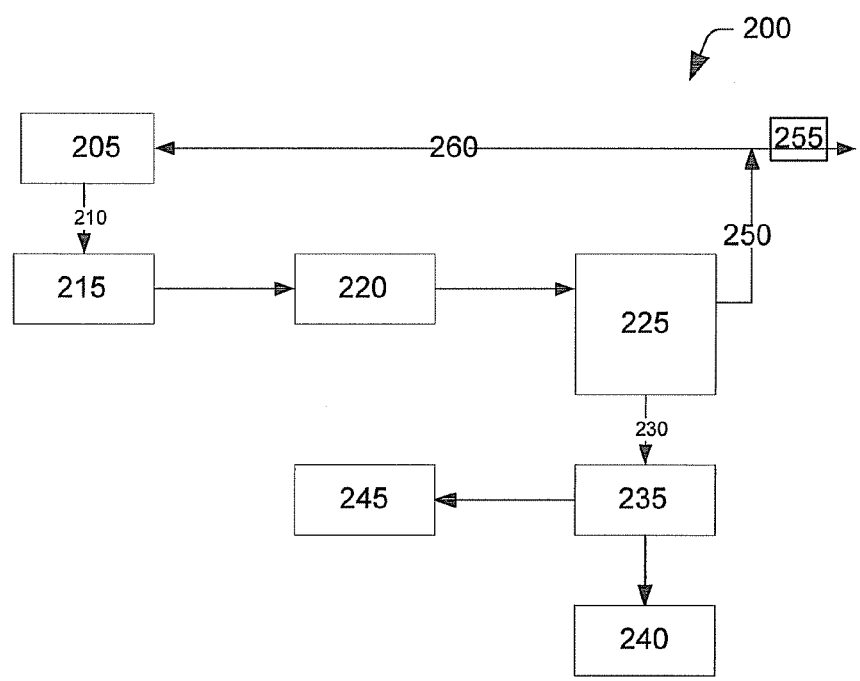
FIG. 2 depicts a pervaporation system in accordance with one aspect of the invention.

FIG. 2 depicts an exemplary pervaporation system 200 that can be employed to separate butanol, or other desirable materials, from a crude fermentation broth containing a valuable organic compound, such as biobutanol. Crude fermentation broth as a feed stream 210 from a feed tank 205 is pumped via pump 215 through a heater 220 to increase its temperature. The fermentation broth is then charged under pressure to a pervaporation module 225 containing a polynorbornene pervaporation membrane. Permeate vapor 230 containing butanol is obtained from the pervaporation module 225, where the butanol vapor is condensed in a condenser 235 with the assistance of a vacuum pump 245. Residual fermentation broth or retentate stream 250 that does not pass through the polynorbornene pervaporation membrane can be either discharged 255 from system 200 or directed to a recycling stream 260 and returned to the feed tank 205.

Supplemental methods that complement the pervaporation process include removing solids from the fermentation broth by centrifugation, filtration, decantation, dephlegmation or the like; increasing the concentration of butanol in the fermentation broth using adsorption, distillation or liquid-liquid extraction.

Butanol from biomass is often referred to as biobutanol. Biobutanol can be produced by fermentation of biomass by the A.B.E. process. The process uses the bacterium of the genus *Clostridium*, such as *Clostridium acetobutylicum*, but others including *Saccharomyces cerevisiae, Zymomonas mobilis, Clostridium thermohydrosulfuricum, Escherichia coli, Candida pseudotropicalis,* and *Clostridium beijerinckii*, can be used. Biobutanol can also be made using genetically modified yeasts for the production of biobutanol from cellulosic materials. The crude fermentation broth containing biobutanol can be advantageously processed by the polynorbornene pervaporation membrane depicted in FIG. 1 and/or the pervaporation system depicted in FIG. 2 to provide concentrated butanol, as compared to the concentration thereof in the crude broth. Not withstanding the above, polynorbornene pervaporation membranes are useful for separation of alcohols other than butanol from the fermentation broths in which they were formed, for example ethanol as shown in Tables 1 and 2, supra. In addition, as carbazole-functionalized norbornene ROMP polymers have been found to have high separation factors for the dehydration of alcohols (Wang et al., "Pervaporation separation of aqueous alcohol solution through a carbozole-functionalized norbornene derivative membrane using living ring-opening metathesis polymerization", *Journal of Membrane Science*, 246 (2005) 59-65), it is anticipated that the vinyl-addition norbornene polymers of the current invention will also exhibit high separation factors while also exhibiting advantageous physical properties, for example Tg, Modulus and hydrolytic stability, as compared to the aforementioned ROMP polymers.

Fermentation broths generally contain a variety of carbon substrates. Examples of such carbon substrates include monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additional examples include one-carbon substrates such as carbon dioxide, or methanol, and two carbon substrates such as methylamine and glucosamine. Generally, the source of carbon utilized in the fermentation broth can vary widely, and it typically driven by the identity of the organism. In addition to the carbon source, fermentation broths can contain suitable minerals, salts, cofactors, buffers and other components, known to those skilled in the art, suitable for the growth of the cultures and promotion of the enzymatic pathway necessary for butanol production. Examples of fermentation broths that are commercially available include Luria Bertani (LB) broth, Sabouraud Dextrose (SD) broth, or Yeast Medium (YM) broth.

As used herein, "butanol" generically refers to n-butanol and/its isomers. In some embodiments in accordance with the present invention, the fermentation broth contains from about 0.1% to about 10% butanol. In other embodiments, the fermentation broth contains from about 0.5% to about 6% butanol. Since the polynorbornene pervaporation membranes described herein are particularly effective at separating butanol from fermentation broths containing a relatively high level of butanol, in yet other embodiments, the fermentation broth contains at least about 1% butanol.

In a process of separating butanol from a crude fermentation broth containing biobutanol, the crude fermentation broth feed is heated to a temperature that facilitates butanol passage through the polynorbornene pervaporation membrane. In one embodiment, the crude fermentation broth feed is heated to a temperature from about 30° C. to about 90° C. In another embodiment, the crude fermentation broth feed is heated to a temperature from about 40° C. to about 80° C. In yet another embodiment, the crude fermentation broth feed is heated to a temperature from about 50° C. to about 70° C.

To facilitate pervaporation, a suitable vacuum can be applied to the vapor chamber of the pervaporation module. In one embodiment, the vacuum applied is from about 0.1 in Hg to about 28 in Hg. In another embodiment, the vacuum applied is from about 1 in Hg to about 25 in Hg.

Other processes include methods of increasing a separation factor for an organic product, such as butanol, as a concentration of the organic product increases in a pervaporation feed stream. Such methods involve using a polynorbornene pervaporation membrane to separate the organic product from the pervaporation feed stream.

As used herein, SF is the separation factor which is a measure of quality of the separation of a first species relative to a second species and is defined as the ratio of the ratio of permeate compositions to the ratio of the feed compositions.

As used herein, flux is the amount that flows through a unit area of a membrane per unit of time.

Flux and SF can also be described by the following equations:

Flux$(J)$=mass/(area·time)

Separation Factor (SF)

$$SF_{12} = \left(\frac{y_1/y_2}{x_1/x_2}\right) = \left(\frac{J_1/J_2}{x_1/x_2}\right) = SF_{VLE}SF_{membrane}$$

$y$ = Permeate concentration, $x$ = Feed liquid concentration

The efficiency of a pervaporation membrane can be readily evaluated in two respects, a separation factor (the ratio of enrichment obtained when the liquid mixture permeates through the membrane) and the flux at which a liquid mixture permeates through the polymeric membrane. Thus the higher the separation factor and velocity factor of a membrane, the higher the separation efficiency of such membrane. Of course this is a very simplified analysis as low separation factors can often be overcome through the use multistage membrane processes and where the flux factor of a membrane is low, often forming such a membrane with a high surface area can overcome low flux. Thus while the separation and flux factors are important considerations, other factors such as a membrane's strength, elasticity, resistance to becoming fouled during use, thermal stability, free volume and the like are also important considerations in selecting the best polymer for forming a pervaporation membrane.

The polynorbornene pervaporation membrane has a suitable separation factor (SF) for butanol to provide an effective means to remove butanol from a fermentation broth. In one embodiment, the polynorbornene pervaporation membrane has a SF for butanol of at least about 5. In another embodiment, the polynorbornene pervaporation membrane has a SF for butanol of at least about 10. In yet another embodiment, the polynorbornene pervaporation membrane has a SF for butanol of at least about 15. In still yet other embodiments, the polynorbornene pervaporation membrane has a SF for butanol of at least about 20, at least about 25, or at least about 30. Moreover, any of the foregoing SFs can be achieved when the concentration of butanol in a feed stream is 2% or higher, 3% or higher, or 4% or higher.

A suitable flux for butanol can be achieved using polynorbornene pervaporation membranes of the present invention to provide an effective means to remove butanol from a fermentation broth. In one embodiment, a flux for butanol of at least about 100 g/m$^2$/hr can be achieved using such polynorbornene pervaporation membranes. In another embodiment, a flux for butanol of at least about 150 g/m$^2$/hr can be achieved; in yet another embodiment, a flux for butanol of at least about 200 g/m$^2$/hr can be achieved and in still another embodiment, a flux for butanol of at least about 250 g/m$^2$/hr can be achieved using such polynorbornene pervaporation membranes. Furthermore, unlike what is generally found using previously known non-polynorbornene pervaporation membranes, any of the foregoing fluxes can be achieved when the concentration of butanol in a feed stream is 2% or higher, 3% or higher, or 4% or higher.

It has been found that polynorbornenes in general are suited for use in forming pervaporation membranes and vinyl addition polymerized polynorbornenes are particularly well suited where the polymerization method allows for polymers to be made that can encompass a variety of pendant groups useful for tailoring the polymer's physical (e.g. Tg, Modulus, free volume, hydrophobicity, hydrolytic stability, and the like) and pervaporation characteristics (e.g., SF and velocity factors). Also, since polynorbornenes, as a class of polymers, have relatively high glass transition temperatures, such polymers can possibly offer the ability of operation as a pervaporation membrane at temperatures higher than possible for currently known membranes. In one embodiment, the polynorbornenes used to make the polynorbornene pervaporation membranes described herein are not ROMP polynorbornenes (ring-opening metathesis polymerization) but instead vinyl addition polynorbornenes.

Generic Polynorbornene Structure I, shown below, is useful to illustrate that the methods for forming such vinyl addition norbornene-type polymers can provide repeating units in the polymer that have a plurality of repeat units having pendant groups selected to provide the resultant polymer with specific properties.

Structure I

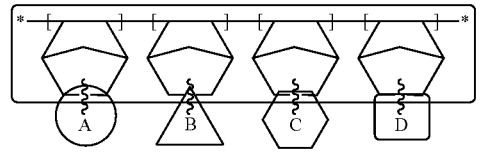

Thus pendant group A might be selected to provide a desirable chemical selectivity to the polymer by incorporating a permeate-like pendant group; pendant group B might be selected to provide an appropriate SF and/or flux by adjusting the polymer's free volume by incorporating an appropriate polyhedraloligosilsesquioxane (POSS) pendant group. In addition, the mechanical properties of the polymer (Tg, Modulus, hydrolytic stability, and the like) might be tailored via pendant group C where, for example, an appropriate alkyl pendant group is provided to some repeating units while surface properties such as the correct amount of hydrophobicity can be tailored by providing an appropriate hydrophobic or hydrophilic pendant group D. It will of course be understood that each of the several pendant groups while having a principal effect on a specific polymer characteristics, will also, generally, have an affect on others of the aforementioned characteristics. As a result, it may be necessary, in some embodiments, to vary more than one pendant group to obtain the properties desired.

Given the considerable interest in the efficient manufacture of renewable fuels such as ethanol and butanol from corn and other high starch or sugar content agricultural products, several available polynorbornenes were tested for selectivity. Initial test methods encompassed treating 1 gram of bulk polymer with 15 grams of a charge liquid having a known concentration of either ethanol or butanol or a mixture thereof. After allowing the charge liquid to remain in contact with the polymer for about 18 hours, the liquid was filtered and the difference in the concentration of alcohol remaining versus the original alcohol concentration was taken to be the amount of alcohol adsorbed. Referring to Tables 1, 2, and 3 shown below, it can be seen that some of the initially tested polymers were effective in absorbing alcohol from the charge liquid, while some were not. Thus, it is believed, such a test can provide an indication that a membrane formed of such a polymer could have selectivity to the alcohol adsorbed. It is noted that sample numbers throughout Tables 1, 2, and 3 refer to specific polymers made, the same sample number in different Tables refer to the same polymer.

TABLE 1

15% EtOH Charge Liquid

| Sample | Polymer | % adsorbed |
| --- | --- | --- |
| #1 | NB | 6.53% |
| #2 | 90/10 - NB/TESNB | 4.93% |
| #3 | 90/10 - NB/decylNB | 3.87% |
| #4 | 75/25 - NB/hexylNB | 3.53% |
| #8 | t-ButyleugenolNB | 1.00% |
| #9 | PENB | 0.60% |
| #10 | 50/50 - AGE/decyl | 0.33% |
| #11 | 70/30 - Decyl/cyclohexyl | 6.47% |
| #12 | 80/20 - Hexyl/MGE | 4.37% |
| #13 | t-ButylesterNB | 4.70% |
| #14 | 90/10 - Butyl/decyl | 3.67% |
| #15 | HexylNB | 0.53% |
| #17 | 70/30 - MCP/SL | 4.00% |
| #18 | 70/30 - HFA/tBuEs | 6.20% |
| #19 | 60/40 - HFA/tBuEs | 5.13% |
| #20 | 50/35/10/5 - MAH/MCP/butyl/SL | 6.27% |
| #21 | HFANB | 4.90% |
| #22 | EPENB | 1.70% |
| #23 | NB-POSS | 4.97% |
| #26 | NB/Glycol/HFA, 65/15/20 | 1.78% |
| #27 | SNB/Glycol/HFA, 50/30/20 | 2.29% |
| #28 | NB/PENB/HFA, 33/33/33 | 1.91% |
| #29 | NB/PENB/HFA, 33/17/6 | 1.22% |
| #30 | NB/PENB/HFA, 67/17/17 | 2.80% |
| #31 | NB/PENB/HFA, 55/20/25 | 3.51% |
| #32 | NB/PENB/HFA, 67/8/25 | 3.29% |
| #33 | NB/PENB/HFA, 58/8/33 | 5.89% |

TABLE 2

5% EtOH Charge Liquid

| Sample | Polymer | % adsorbed |
| --- | --- | --- |
| #1 | NB | 6.80% |
| #2 | 90/10 - NB/TESNB | 0.30% |
| #11 | 70/30 - Decyl/cyclohexyl | 6.20% |
| #18 | 70/30 - HFA/tBuEs | 4.00% |
| #19 | 60/40 - HFA/tBuEs | 6.40% |
| #20 | 50/35/10/5 - MAH/MCP/butyl/SL | 9.20% |
| #26 | NB/Glycol/HFA, 65/15/20 | 3.40% |
| #27 | NB/Glycol/HFA, 50/30/20 | 1.80% |
| #28 | NB/PENB/HFA, 33/33/33 | 4.50% |
| #33 | NB/PENB/HFA, 58/8/33 | 6.60% |

TABLE 3

5% Butanol Charge Liquid

| Sample | Polymer | % adsorbed |
| --- | --- | --- |
| #2 | 90/10 - NB/TESNB | 16.9% |
| #3 | 90/10 - NB/decylNB | 18.3% |
| #4 | 75/25 - NB/hexylNB | 18.8% |

TABLE 3-continued

5% Butanol Charge Liquid

| Sample | Polymer | % adsorbed |
| --- | --- | --- |
| #5 | 55/25/20 - Hexyl/TMS/pFcinnamate | 8.5% |
| #7 | 40/30/30 - PENB/epoxy/decyl | 13.3% |
| #8 | t-ButyleugenolNB | 11.8% |
| #9 | PENB | 6.1% |
| #10 | 50/50 - AGE/decyl | 12.6% |
| #11 | 70/30 - Decyl/cyclohexyl | 24.2% |
| #12 | 80/20 - Hexyl/MGE | 10.6% |
| #13 | t-ButylesterNB | 22.0% |
| #14 | 90/10 - Butyl/decyl | 9.5% |
| #15 | HexylNB | 7.5% |
| #17 | 70/30 - MCP/SL | 29.9% |
| #18 | 70/30 - HFA/tBuEs | 27.1% |
| #19 | 60/40 - HFA/tBuEs | 30.0% |
| #20 | 50/35/10/5 - MAH/MCP/butyl/SL | 29.8% |
| #21 | HFANB | 45.9% |
| #23 | 33/33/33 - HFA/NB/DecylNB | 24.2% |
| #34 | 49/51 - BuNB/EtOcoumarinNB | 25.5 |
| #35 | 29/71 - DecNB/EtOcoumarinNB | 22.8 |
| #36 | 29/71 - BuNB/EtOcoumarinNB | 27.4 |
| #37 | 100 - EtOcoumarinNB | 24.9 |
| #38 | 50/50 - $CH_2C_6F_5NB/DMMINB$ | 35.6 |
| #39 | 70/30 - MeOAcNB/AGENB | 32.8 |
| #40 | 30/70 - AONB/MeOAcNB | 26.2 |

As seen in the Tables 1 and 2, while some ethanol was adsorbed by most polymers, in no case was the percent adsorbed as high as 10%. While in Table 3, the polymer of sample 21 adsorbed in excess of 40% of the butanol and the polymers of samples 1, 11, 13, 17-20, and 34-40 each adsorbed in excess of 20% of the butanol originally present in the charge liquid. While the above results indicate that polynorbornenes can be useful for both ethanol and butanol absorption, the greater selectivity to butanol directed the further evaluation of polynorbornenes as pervaporation membranes to using a butanol/water charge liquid. The results of this second set of screenings, performed in the same manner used for the first screening shown in Tables 1-3 but using a 5% butanol charge liquid, are shown in Table 4.

TABLE 4

5% Butanol Charge Liquid

| Sample | Polymer | % BuOH Adsorption |
| --- | --- | --- |
| A | HFANB/tBuEs (70/30) | 27.1% |
| B | NB/TESNB (90/10) | 16.9% |
| C | DecylNB/cyclohexylNB (70/30) | 24.2% |
| D | NB | 20.9% |
| E | NB/PENB/HFANB (33/33/33) | 44.3% |

As seen in Table 4, samples A, C and E gave the best results. Given the results shown for the two HFANB containing polymers in the above table, an adsorption ratio greater than 5 with respect to butanol, the polymer of Sample E was selected for preparing a membrane to be further evaluated and compared to reported selectivity data for currently known pervaporation membranes. It will be noted that the adsorption ratio is calculated as the percent of butanol adsorbed by the polymer divided by the original concentration of butanol in the charge liquid.

Referring to Table 5, below, data is presented for a membrane made from the polymer of Sample E and for membranes made from both polydimethylsiloxane (PDMS) and Silicalite (an aluminum-free silica-based zeolite). It should be noted that for each of the currently known materials, the data shown was obtained from published reports using butanol laced charge liquids as noted below the table. It should be further noted that the PDMS sample was a thin, essentially non porous membrane and the Silicalite, due to its structure, was a porous material thus enhancing the velocity of permeation through that membrane as compared to a relatively thick, dense, essentially non-porous membrane as was the case for the Sample E membrane. Additionally, it is generally known that results for separation factor, are often higher where a charge liquid having a lower concentration of the organic material to be separated is used. Thus, the results shown in Table 5 are, it is believed, quite remarkable and a strong indication that pervaporation membranes made from polynorbornenes can be commercially viable once such polymers are tailored and a process for forming membranes having porous or other structures is more fully developed. It should be noted that experimental data is presented below for the forming of the polymer of Sample E and the dense membrane thereof, see Sample E Experimental. Additionally, the method of testing such a membrane is described. Finally, it should be noted that Table 5 also displays data for what is believed to be an "Ideal" pervaporation membrane. Comparing this data to that of the membrane formed form the Sample E polymer is particularly encouraging.

TABLE 5

Proof-of-concept data for PNB as membrane material for butanol pervaporation

| Membrane material | Structure | Separation Factor (weight basis) | Flux (g/m²/hr) |
|---|---|---|---|
| Sample E | Thick Film | 30 ± 5** | 285 ± 40 |
| PDMS† | Thin Film | 27* | Not reported |
| Silicalite† | Membrane | 19** | Not reported |
| Ideal material | — | >40 | >1000 |

*At 3% aqueous butanol concentration in feed.
**At 5% aqueous butanol concentration in feed.
†L. M. Vane, J. Chem. Technol. Biotechnol. 2005, 80, 603.

Definitions
  thf: Tetrahydrofuran CAS: [109-99-9]
  DME: 1,2-Dimethoxyethane CAS: [110-71-4]
  RT: room temperature
  PGMEA: propylene glycol methyl ether acetate CAS: [108-65-6]
  MGENB: methyl glycidyl ether norbornene CAS: [3188-75-8]
  DeNB: 5-decyl-2-norbornene CAS: [22094-85-5]
  PENB: phenethyl norbornene CAS: [29415-09-6]
  TMSNB: trimethoxysilyl norbornene CAS: [7538-46-7]
  TESNB: triethoxysilyl norbornene CAS: [18401-43-9]
  MeOAcNB: 5-norbornene-2-methanol acetate CAS: [10471-24-6]
  HFANB: hydroxyhexafluoroisopropyl norbornene CAS: [196314-61-1]
  TFSNB: N-(Bicyclo[2.2.1]hept-5-en-2-ylmethyl)-1,1,1-trifluoromethanesulfonamide CAS: [287923-92-6]
  tBuEsNB: Bicyclo[2,2,1]hept-5-ene-2-tert-butylcarboxylate CAS: [154970-45-3] and
  Mw: Molecular weight.

The polynorbornenes described herein are the result of a vinyl addition polymerization reaction that encompasses one or more "polycycloolefin," "polycyclic," or "norbornene-type" monomers that are inclusive of at least one norbornene moiety in accordance with Structure 1 shown below. After the polymerization reaction, the polymeric material formed from such a monomer encompasses at least one repeat unit in accordance with Structure 2, also shown below:

Some embodiments of the present invention may include repeat units derived from norbornene-type monomers having an acid labile protected pendant group. Such monomers are represented by Formula A, below:

Formula A

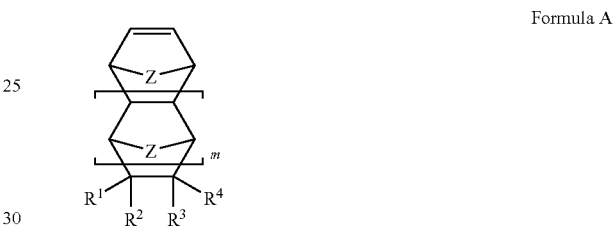

where m and Z are defined above and where at least one of $R^1$, $R^2$, $R^3$, or $R^4$, independently, is an acid labile protected pendant group that is cleavable by, for example, an acid generated from a photoacid generator. Any known acid labile group known to the literature and to the art can be utilized in the present invention such as those set forth herein with regard to Formula A.

The remaining one or more $R^1$, $R^2$, $R^3$, or $R^4$, groups, independently, can be hydrogen, or a hydrocarbyl having from 1 to about 20 carbon atoms, or halogens selected from F, Cl or Br, or a hydrocarbyl having from 1 to about 20 carbon atoms substituted at any hydrogen atom with an O, S, N, or Si, and the like, or a fluorinated hydrocarbyl having from 1 to about 20 carbon atoms wherein each carbon atom, independently, is substituted with 0, 1, 2, or 3 fluorine atoms.

In some embodiments, the acid labile group is a fluorinated carbinol moiety having from 1 to about 20 carbon atoms wherein each carbon atom, independently, is substituted with 0, 1, 2, or 3 fluorine atoms and the oxygen atom is protected by an acid labile group (i.e., blocking or protective groups) that are cleavable by acids generated from a photoacid generator. Any acid labile group known to the art and to the literature can be employed in the present invention. Advantageous fluorinated groups include, among others, —((CH$_2$)$_n$O)$_{n^*}$—CH$_2$—C(OR')(CF$_3$)$_2$ and —O—((CH$_2$)$_n$O)$_{n^*}$—CH$_2$—C(OR')(CF$_3$)$_2$ where n and n* are integers from 0 to about 10, and where R' is the acid labile group. R' includes, but is not limited to, —CH$_2$OCH$_3$ (dimethyl ether), —CH$_2$OCH$_2$CH$_3$ (methyl ethyl ether), —C(CH$_3$)$_3$, —Si(CH$_3$)$_3$, —CH$_2$C(O)O(t-Bu), isobornyl, 2-methyl-2-adamantyl, tetrahydrofuranyl, tetrahydropyranyl, 3-oxocyclohexanonyl, mevalonic lactonyl, dicyclopropylmethyl (Dcpm), or dimethylcyclopropylmethyl (Dmcp) groups, or R' is —C(O)OR" where R" is —C(CH$_3$)$_3$, —Si(CH$_3$)$_3$, isobornyl, 2-methyl-2-adamantyl, tetrahydrofuranyl, tetrahydropyranyl, 3-oxocyclohexanonyl, mevalonic lactonyl, Dcpm, or Dmcp groups, or combinations thereof.

In some embodiments of the present invention, Formula A is represented by Formula A1, below

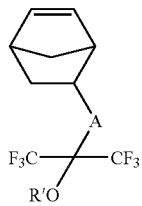

Formula A1 where A is a bridging group such as a $C_1$ to $C_5$ alkyl group or $((CH_2)_n\cdot O)_m$ where n and m independently are 1 to 4 and R' are as previously defined. More specifically, exemplary monomers encompassing an acid labile protected pendant group include:

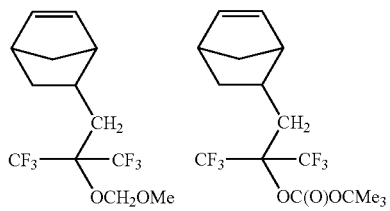

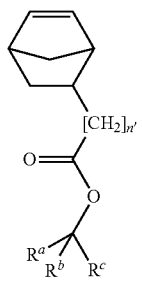

Other norbornene-type monomers in accordance with Formula A are represented by Formula A2, below:

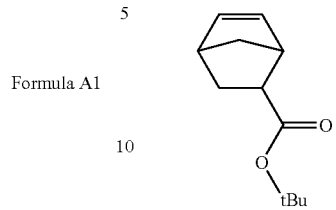

Formula A2 where n' is an integer 1 to about 5 and $R^a$, $R^b$, and $R^c$, independently, represent linear or branched hydrocarbyl groups from $C_1$ to about $C_{20}$ or where $R^a$ and $R^b$ taken together along with the common carbon to which they are attached can represent saturated $C_4$ to $C_{12}$ cyclic groups.

An exemplary norbornene-type monomer in accordance with Formula A2 encompasses:

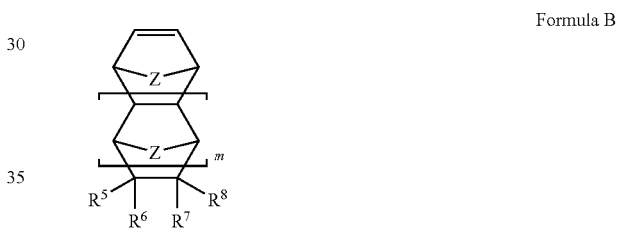

where tBu is a tertiary butyl group.

Some embodiments in accordance with the present invention are polymers that encompass two or more different types of repeat units derived from norbornene-type monomers, where at least one such type of repeat unit has a polyhedral oligosilsesquioxane (POSS) pendant group. Such polyhedral oligosilsesquioxane containing repeat units are derived from norbornene-type monomers represented by Formula B, below.

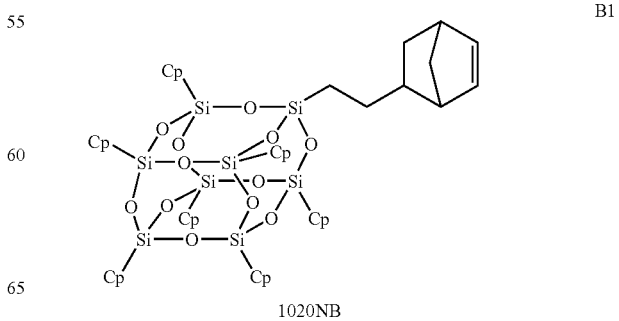

Formula B where m is an integer from 0 to about 5; Z represents $-(CH_2)_p-$, $-O-$, $-S-$, or $-NH-$, and p is either 1 or 2. Further, at least one of $R^5$, $R^6$, $R^7$, or $R^8$, independently, is a polyhedral oligosilsesquioxane moiety and each of the remaining $R^5$, $R^6$, $R^7$, or $R^8$ groups, independently, is a hydrogen atom, or a linear or branched hydrocarbyl group having from 1 to about 20 carbon atoms. Monomers in accordance with Formula B are available from Hybrid Plastics of Hattiesburg, Miss., and include, but are not limited to, Formulae B1, B2, B3, B4, B5 and B6, below:

1020NB

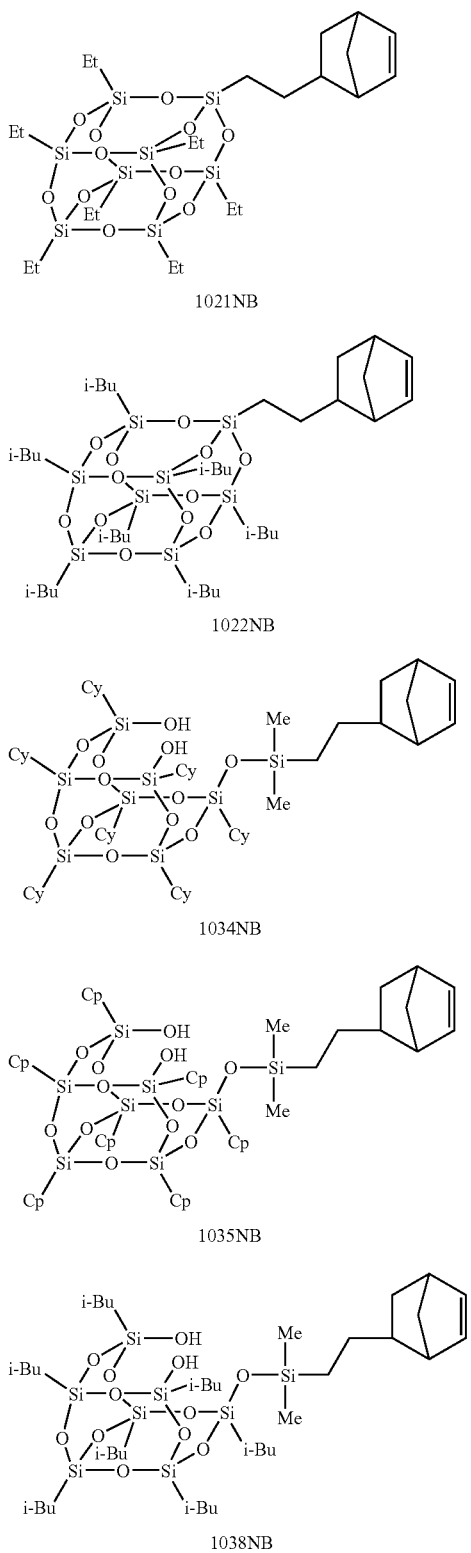

where Cp is cyclopentyl, Cy is cyclohexyl, Me is methyl, Et is ethyl and i-Bu is iso butyl.

In addition, some embodiments in accordance with the present invention include repeat units derived from norbornene-type monomers having pendant groups that are exclusive of polyhedral oligosilsesquioxane groups, acid labile protected groups and crosslinking capable groups. Such monomers are represented by Formula C, below:

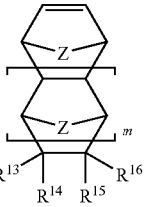

Formula C where m and Z are defined as above, and where substitutents $R^{13}$, $R^{14}$, $R^{15}$ and $R^{16}$, are each independently hydrogen, a linear or branched $C_1$ to $C_{10}$ alkyl or a neutral substituent selected from the group of substituents consisting of halogens selected from F, Cl or Br, —$(CH_2)_n$—$C(O)OR^{17}$, —$(CH_2)_n$—$OR^{18}$, —$(CB_2)_n$—$OC(O)R^{17}$, —$(CH_2)_n$—$OC(O)OR^{17}$, —$(CH_2)_n$—$C(O)R^{18}$, —$(CH_2)_nC(R^{19})_2CH(R^{19})(C(O)OR^{20})$, —$(CH_2)_nC(R^{19})_2CH(C(O)OR^{20})_2$, —$C(O)O$—$(CH_2)_n$—$(O$—$(CH_2)_n)_p$—$OR^{18}$ and —$(CH_2)_n$—$(O$—$(CH_2)_n)_p$—$OR^{18}$, where n is independently an integer from 0 to 10, p is independently an integer from 0 to 6, B can be hydrogen or a halogen (i.e., fluorine, chlorine, bromine, and/or iodine), $R^{19}$ can independently be hydrogen, a halogen such as fluorine, chlorine, bromine or iodine, a linear or branched $C_1$ to $C_{10}$ alkyl group or $C_4$ to $C_{12}$ cycloalkyl group or a linear or branched $C_1$ to $C_{10}$ halogenated alkyl group or $C_4$ to $C_{12}$ halogenated cycloalkyl group, $R^{18}$ can independently be hydrogen, a linear or branched $C_1$ to $C_{10}$ alkyl group or $C_4$ to $C_{12}$ cycloalkyl group or a linear or branched $C_1$ to $C_{10}$ halogenated alkyl group or halogenated $C_4$ to $C_{12}$ cycloalkyl group, $R^{20}$ is not readily cleavable by a photoacid generator and can independently be a linear or branched $C_1$ to $C_{10}$ alkyl group or $C_4$ to $C_{12}$ cycloalkyl group or a linear or branched $C_1$ to $C_{10}$ halogenated alkyl group or $C_4$ to $C_{12}$ halogenated cycloalkyl group, and $R^{17}$ is not readily cleavable by a photoacid generator and can independently be hydrogen, linear or branched $C_1$ to $C_{10}$ alkyls or halogenated alkyls, a monocyclic or polycyclic $C_4$ to $C_{20}$ cycloaliphatic or halogenated cycloalkyl moiety, a cyclic ether, a cyclic ketone or a cyclic ester (lactone), where each of the cyclic ether, ketone and ester can be halogenated or not. Exemplary cycloaliphatic moieties include, but are not limited to, unsubstituted cyclopropyl, cyclobutyl, cyclopentyl, cyclohexyl groups as well as 1-adamantyl and 1-norbornene moieties. In addition, in some embodiments, repeat units of the present invention are derived from monomers represented by Formula A1, where R' is a hydrogen (all other variable as defined in Formula A1).

It will be noted that generally polymers in accordance with the present invention encompass one or more types of repeat units derived from monomer types represented by Formulae A, B, and C, such polymers generally encompass one or more repeat units derived from a monomer in accordance with Formula A and at least one other type of repeat unit derived from a monomer in accordance with Formulae B and/or C. Other advantageous embodiments in accordance with the present invention encompass appropriate homopolymers and/or copolymers encompassing repeat units derived from monomers in accordance with Formulae B and/or C.

The norbornene-type polymers of embodiments in accordance with the present invention are prepared by vinyl addition polymerization using neutral or cationic palladium based catalysts such as set forth in U.S. Pat. No. 6,455,650, or nickel based catalysts as set forth in U.S. Pat. No. 6,232,417. The pertinent parts of these patents are incorporated herein by reference. Exemplary palladium catalysts encompass, among others, trans-[Pd(NCMe)(OAc)(P(i-propyl)$_3$)$_2$]B(C$_6$F$_5$)$_4$, trans-[Pd(NCC(CH$_3$)$_3$)(OAc)(P(i-propyl)$_3$)$_2$]B(C$_6$F$_5$)$_4$, trans-[Pd(OC(C$_6$H$_5$)$_2$)(OAc)(P(i-propyl)$_3$)$_2$]B(C$_6$F$_5$)$_4$, trans-[Pd(HOCH(CH$_3$)$_2$)(OAc)(P(i-propyl)$_3$)$_2$]B(C$_6$F$_5$)$_4$, trans-[Pd(NCMe)(OAc)(P(cyclohexyl)$_3$)$_2$]B(C$_6$F$_5$)$_4$, Pd(OAc)$_2$(P(cyclohexyl)$_3$)$_2$, Pd(OAc)$_2$(P(i-propyl)$_3$)$_2$, Pd(OAc)$_2$(P(i-propyl)$_2$(phenyl))$_2$, trans-[Pd(NCMe)(OAc) (P(cyclohexyl)$_2$(t-butyl))$_2$]B(C$_6$F$_5$)$_4$, and mixtures thereof.

Exemplary nickel catalysts encompass, among others, (toluene)bis(perfluorophenyl)nickel, bis(tetrahydrofuran)bis (perfluorophenyl)nickel, (dimethoxyethane)bis(2,4,6-tris (trifluoromethylphenyl)) nickel, bis(dioxane)bis(perfluorophenyl)nickel, bis(ethylacetate)bis(perfluorophenyl)nickel and mixtures thereof.

The polynorbornene pervaporation membranes can be in any suitable form to effect separation of a desirable material, for example butanol, from a fermentation broth. Examples include spiral wound modules, fiber membranes including hollow fiber membranes, tubular membranes, and flat sheet membranes, such as in a plate and frame configuration, a supported or unsupported dense film, or a thin film composite.

When the polynorbornene pervaporation membranes are in an unsupported dense film form, the thickness of the dense film is from about 1 micron to about 500 microns. In another embodiment, the thickness of the dense film is from about 5 microns to about 100 microns.

When the polynorbornene pervaporation membranes are in the form of a thin film composite, such membranes can be thinner that unsupported membranes, for example as thin as about 0.1 microns. Further, the membrane contains at least one layer of polynorbornene and at least one layer of a non-polynorbornene component. Such composites can contain multiple layers of polynorbornene pervaporation membranes and multiple layers of non-polynorbornene component. Examples of the non-polynorbornene component include non-polynorbornene polymers and inorganic materials. Examples of non-polynorbornene polymers include polyethylenes including Tyvek®, polypropylenes, polyesters, polyimides, polycarbonates, polytetrafluoroethylene, poly(vinylidene fluoride) (PVDF), poly(methyl methacrylate) (PMMA), mixed co- and ter-polymers thereof, and the like. Examples of inorganic materials include zeolites, glass frits, carbon powder, metal sieves, metal screens, metal frit, and the like. In one aspect, the non-polynorbornene polymers and/or the inorganic materials have filtering characteristics and can be referred to as non-polynorbornene filtering components.

The polynorbornene used to make the polynorbornene pervaporation membranes has a Mw of at least about 5,000. In another embodiment, the polynorbornene used to make the polynorbornene pervaporation membranes has a Mw of at least about 50,000. In yet another embodiment, the polynorbornene used to make the polynorbornene pervaporation membranes has a Mw of at least about 500,000. Generally, the larger the Mw, the more suitable the polynorbornene is for use in unsupported forms of the polynorbornene pervaporation membranes.

General Preparation of Norbornene Polymers

One or more norbornene monomers can be dissolved in one or more organic solvents and charged to a reactor vessel. Air and/or dissolved water are removed.

A catalyst solution is added to the monomer solution. Using various techniques including extraction and the like a polynorbornene polymer is collected and dried.

Exemplary polymerization processes are described in published U.S. Patent Publication No. 20060020068 A1 at paragraphs [0053] and [0057], such paragraphs, and the documents referenced therein, are herein incorporated by reference. Other exemplary polymerization processes are described in U.S. Pat. No. 5,468,819 and U.S. Patent Publication No. 20070066775, also incorporated herein by reference.

Preparation of the Sample E Polymer (Nb/Penb/Hfanb)

NB (49.8 g, 0.5 mol), PENB (105.0 g, 0.5 mol) and HFANB (145.3 g, 0.5 mol) were dissolved in a mixture of toluene and 1,2-dimethoxyethane (85/15) and then charged to 3 liter reactor vessel. The vessel and solution was sparged with N$_2$ for one hour to remove any air and dissolved water. A nickel catalyst solution was prepared in a dry-box by dissolving 4.8 g of NiArf (0.01 mol) in 49.2 g of anhydrous ethyl acetate. A water bath surrounding the reactor was controlled to have a temperature of 25° C. The catalyst solution was added to the monomer via a dry cannula syringe. The monomer to NiArf ratio was 160:1. After the reaction mixture was stirred for four hours with jacket controlled to be 25° C., a viscous polymer solution with a color of dark orange was obtained. To dilute the product solution, 200 g of tetrahydrofuran was added. After the tetrahydrofuran and the product mixed, 172.1 g de-ionized water and 172.1 g per-acid solution, which included 59.6 g (1 mol) glacial acetic acid and 112.5 g (1 mol) 30% hydrogen peroxide, were added and stirred overnight. With the jacket temperature controlled to be 60° C., the two phases started to separate after 20 minutes. After acid wash, NiArf catalyst was transferred to acid layer from polymer phase, and then drain off the acid layer. Next, 450 g deionized water and 150 g iso-propanol were added, stirred for ten minutes, allowed to separate, and drained. Repeated the water wash and draining procedure for three times. The polymer solution was precipitated into 80/20 MeOH/water mixture and filtered through a filter paper. The white polymer powder was collected and dried in a vacuum oven at 70° C. overnight. $^{13}$C NMR analysis confirmed the terpolymer composition as NB/PENB/HFANB 28/43/29.

It should be noted that the method of forming the polymer of Sample E, presented above, is not the only method for making such a polymer. Also, it should be noted that such polymer was not the only polymer evaluated and data for the several other polymers formed into membranes is presented in Other Polymer Experimental section below, after the Sample E Experimental section. Thus the polymer embodiments in accordance with the present invention can also be prepared by addition polymerization of the appropriate monomers in the presence of a single or multi-component Group VIII transition metal catalyst performed in an appropriate solvent.

Preparation of a Dense Membrane

Single Thickness Film: A polynorbornene is dissolved in an organic solvent to make a solution which is then filtered. After filtration, trapped gas can be removed. The polymer is poured onto a substrate and pulled to form a film. The film is then simply dried and removed from the substrate and ready for use.

For example, 12 g of the above formed polymer was dissolved in 88 g mesitylene to make a solution (Solution P) which was filtered through a 5 micron nylon filter disc pressurized to between 60~80 psig. After filtration, the solution was allowed to roll overnight on a jar roller to remove trapped gas introduced during the filtration. The polymer was poured onto a glass substrate in the clean room and pulled, using a Gardner Film Casting Knife to form a film having an essentially uniform thickness. The film was allowed to dry in the air overnight and then removed from the substrate by immersing the substrate and film into a warm water bath (40~50° C.) and after a few minutes, peeling the film carefully from the substrate. The film was peeled off from the glass panel while immersed in the warm water and then wiped with a lint-free cloth to remove excess water.

Double Thickness Film: Double thickness films are prepared in a similar manner to the single film except that a second layer of the solution is provided over the first film before the first film is removed from substrate, and then pulling the second film. After the second pass was pulled, the double film was dried and then removed from the substrate and ready for use.

For example, the single thickness film example described above is followed, except that about 5 hours after the first film casting, a second layer is provided by pouring a second aliquot of Solution P over the first film and pulling it as was done above with a Gardner Film Casting Knife. After the second pass was pulled, the film was dried in the air overnight.

Membrane Film Making: A polynorbornene is dissolved in an organic solvent to make a polymer solution. The polymer solution is filtered, then the polymer solution is treated to remove the trapped bubbles. The polymer solution is applied into a polymer web to make a reinforced membrane, on a sheet to make supported membrane, or on a substrate panel to make a non-supported membrane. After the polymer solution is pulled, the membrane is treated to create porosity therein. The porous membrane can be stored in a water bath until use.

For example, 12 g NB/NB-Phenylethyl/NB-Hexafluoro alcohol polymer (Mw: 515,293 g/mol) was dissolved in 88 g of BuOH/THF (1:3) mixture to make 12% polymer solution. Following this, the polymer solution was filtered through 5 micron Nylon filter disc under a pressure of 60~80 psig. After filtration, the polymer solution was placed on a roller overnight to remove the trapped bubble in order to ensure the quality of the membrane. The cleaned polymer solution can be poured into polyester web to make a reinforced membrane, on a Tyvek® sheet to make supported membrane, and on a glass panel to make a non-supported membrane. After the polymer solution was pulled by Gardner Film Casting Knife, the membrane was immediately coagulated into water preheated at 50° C. to create porosity therein. After 5-10 minutes, the porous membrane was immersed in a fresh water bath and maintained at 50° C. until used.

Pervaporation Test

The membrane was cut into 2 inch circles for installation into a capsule that was then placed in the pervaporation testing device. The charge liquid in the testing device was heated to 70° C., and circulated therein for 10 minutes to check for any leaking. After this check was completed a vacuum was pulled on the dry side of the membrane and any permeate was collected into a cooled trap. The system was allowed to run for three hours, collected permeate was warmed to room temperature and evaluated.

Evaluation of the Permeate

The room temperature permeate, having separated into a two-phase liquid, was weighed and found to be 2.2 g. To this permeate, 0.4 g of MeOH was added to make the phases miscible, thus providing a single phase permeate. The single phase permeate (1 gram) was added to a GC sampling vial containing 0.02 g of PGMEA and mixed thoroughly. A sample from the vial was then injected into a Gas Chromatograph where the % butanol was determined by evaluating the area of the butanol peak with respect to the PGMEA standard.

In addition to forming a membrane supported on Tyvek® sheet, the possibility of forming hollow fibers that encompass the polynorbornenes of embodiments of the present invention was evaluated. The following procedure was used to successfully form hollow fibers for further evaluation.

Hollow Fiber Membrane Film Making

A polynorbornene is dissolved in an organic solvent and filtered to remove particles. This solution is then pressure transferred through the outer bore of a spinneret while a mixture of a solvent and salt is simultaneously pressure transferred through the inner bore of the spinneret. These pressure transferred materials were directed to a precipitating bath to provide hollow fibers. The dimensions of the hollow fibers can be controlled by the size of the inner/outer bores and the pressures under which the solutions are transferred.

For example, PNB (33/33/33 NB/PENB/HFANB) was dissolved in 75/25 THF/butanol solution at 11.5 wt % and filtered through a 100 micron filter to remove particles. This solution was then pressure transferred through the outer bore of a double-bore spinneret having an outside diameter of 1.0 mm and an inside diameter of 0.5 mm while a mixture of 20/80 MeOH/5% LiCl(aq) solution was simultaneously pressure transferred through the inner bore of the spinneret. These pressure transferred materials were directed to a precipitating bath (20/80 MeOH/water) where hollow fibers were observed and evaluated. The dimensions of the hollow fibers removed from the bath were confirmed by SEM as having a 0.5 mm diameter and 0.035 mm wall thickness.

Forming Thin Film Composite Hollow Fibers

Generally speaking, a polynorbornene polymer was dissolved in a suitable solvent (e.g., mesitylene) at a suitable concentration (e.g., 5 wt %) and filtered through a 100 micron filter to remove particles. A hollow fiber microfiltration or ultrafiltration membrane (e.g., 0.1 micron PVDF or 3000 MWCO polysulfone) with the inner lumen blocked off was dipped into the polynorbornene solution and then pulled out of the solution. The solvent was removed by drying the fiber at suitable conditions (e.g., 23-60° C. for 0.5-12 hrs). These thin film composite hollow fibers were examined using SEM. The SEM images confirmed that 3-7 micron thick dense films of polynorbornene were formed on the outside of the hollow fibers.

Sample E Experimental

PVP (polyvinyl pyrolidone) blending effect: A 15% TS solution NB/PENB/HFANB in BuOH/THF (1/3) was blended with PVP at different concentrations, 0, 25, 33, 50, 75 and 100 phr. Then the membrane with no support was cast, coagulated into 25/75 MeOH/water at room temperature and soaked in fresh water. As shown in Table 1, 0 phr membrane exhibited a translucent color and a flexible mechanical property. With the concentration of PVP increased, mechanical property appeared weak. In addition, the membrane specimens showed a pattern in their SEM cross section images (in FIG. 3). 0 phr membrane was extremely thin, 25 μm, and 25 phr membrane looked thicker, ~85 μm. All other four membranes had the thickness of 110~150 μm measured by SEM. At high magnification images (in FIGS. 4 and 5), 0 phr membrane exhibited a particulate nature, while all others had a coral-like microstructure with a channel organization. The conclusion is that PVP blending at 33-100 phr results in significant morphology changes (porosity) compared to without blending.

Figure 6:
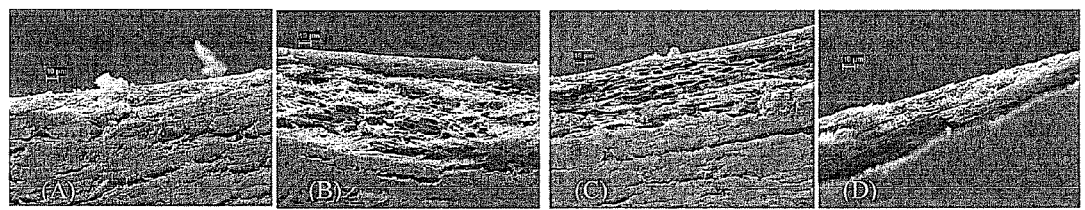
Figure 7:
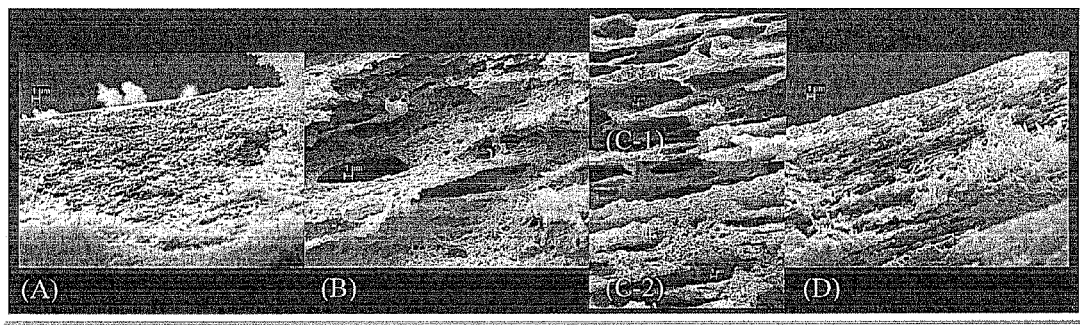

Precipitation temperature effect: A PNB solution with 100 phr PVP was cast on Tyvek® and coagulated into water at various temperature, 20, 40, 50 and 60° C. The appearance of the membrane supported by Tyvek® was observed and listed in Table 2. The PNB, which was leached at 20° C., cracked and peeled off from Tyvek® support, while other membrane specimens remained intact, although the Tyvek® was slightly distorted due to interaction with the THF in the polymer solution. As shown in FIGS. 6 and 7, the morphology of these four membranes from the SEM cross section pictures exhibited a pattern with temperature. The microstructure of the 20° C. membrane sample was coral-like, with a slightly laminar appearance with no channels. The 40° C. membrane had a lacy structure with channels, and the lacy "walls" around the channels were rather dense with some sub-micron channels. The 50° C. membrane was highly channeled, and it also had a different structure adjacent to the Tyvek® than in the bulk. It is likely that the channels adjacent to the Tyvek® might collapse during the coagulation procedure. The 60° C. membrane exhibited a coral-like structure with somewhat laminar. It is highly suspected that the channel microstructure might collapse to some extent. The conclusion is drawn that for 100 phr solution, coral-like structure may start to form a channel with temperature goes up from 20° C. to 50° C. When temperature reaches some level (60° C.), the channel is likely collapsing. In conclusion, "annealing" can be used to improve the mechanical properties without negatively affecting the microporous structure. For the first time, we have prepared porous PNB membranes with sufficient strength for permeability and separation factor testing.

Temperature effect for polyester web-reinforced membrane: The PNB solution with 0 phr PVP was cast into the heavy polyester web (ReeMay 2024, 2.1 oz per square yard, 12 mil thick) and leached into water at two different temperatures 20° C. and 60° C. The membrane specimens were submitted for SEM cross section and surface images (shown in the Table 3). From the SEM surface images, one surface exhibit smooth and uniformly covered, while the other was less uniform. The smooth surface appeared cracking in some areas, in FIG. 8 (A-2), even at high temperature in FIG. 8 (B). At high magnification, in FIG. 9, on the smooth surface, whether intact or cracked, there was evidence of porosity that was uniformly circular and sub-micron with a rather narrow size distribution. Although uniform circular submicron pores and SEM cross section images, in FIG. 10, are desirable, the cracking on the smooth surface (thin film) harms the quality of the membrane causing the leaking during pervaporation test. "Annealing" at 60° C. might decrease the cracking but could not avoid the cracking completely for polyester-reinforced PNB techniques, so we decided not to move forward on this polyester-reinforced approach. However, we did learn that SEM is an excellent method for checking the quality of the surface for membrane; optical microscopy is insufficient.

TABLE 6

"Appearance of membranes with various PVP blending"

| PVP blending in PNB solution (phr) | Color | Mechanical Properties |
|---|---|---|
| 0 | Translucent | Flexible |
| 25 | White | Acceptable |
| 33 | White | Crack appears |
| 50 | White | Crack appears |
| 75 | White | Crack appears |
| 100 | White | Crack appears |

Figure 3:
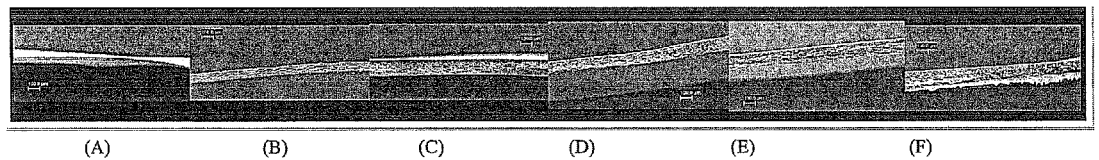
FIGS. 3 to 10 are electron micrographs of various polynorbornene pervaporation membranes in accordance with various aspects of the invention.

FIG. 3 depicts electron micrographic images (magnification: 10 μm) of the cross section of membranes with various PVP blending. (A) 0 phr; (B) 25 phr; (C) 33 phr; (D) 50 phr; (E) 75 phr; (F) 100 phr.

Figure 4:
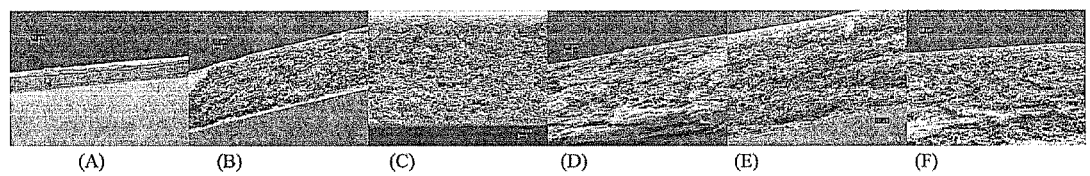

FIG. 4 depicts electron micrographic images (magnification: 1 0pm) of the cross section of membranes with various PVP blending. (A) 0 phr; (B) 25 phr; (C) 33 phr; (D) 50 phr; (E) 75 phr; (F) 100 phr.

Figure 5:
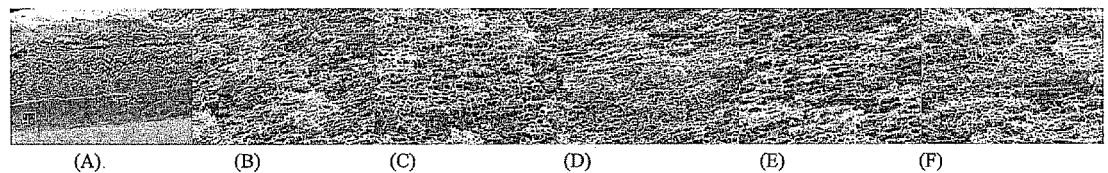

FIG. 5 depicts electron micrographic images (magnification: 1 μm) of the cross section of membranes with various PVP blending. (A) 0 phr; (B) 25 phr; (C) 33 phr; (D) 50 phr; (E) 75 phr; (F) 100 phr.

TABLE 7

"Temperature effect of PNB membrane on Tyvek ®"

| Operation Temperature (° C.) | Observations |
|---|---|
| 20 | Cracks and peelings appear |
| 40 | No peelings, Tyvek ® is a little wavy |
| 50 | No peelings, Tyvek ® is a little wavy |
| 60 | No peelings, Tyvek ® is a little wavy |

FIG. 6 depicts electron micrographic images (magnification: 10 μm) of the cross section of membranes supported by Tyvek®. The membranes were coagulated at various temperatures. (A) 20° C.; (B) 40° C.; (C) 50° C.; (D) 60° C.

FIG. 7 depicts electron micrographic images (magnification: 1 μm) of the cross section of membranes supported by Tyvek®. The membranes were coagulated at various temperatures. (A) 20° C.; (B) 40° C.; (C-1) 50° C., areas in the bulk; (C-2) 50° C., areas adjacent to the Tyvek®; (D) 60° C.

TABLE 8

"Temperature effect of polyester reinforced PNB"

| Operation Temperature (° C.) | SEM |
|---|---|
| 20 | Cross section and surfaces (both sides) |
| 60 | Cross section and surfaces (both sides) |

Figure 8:
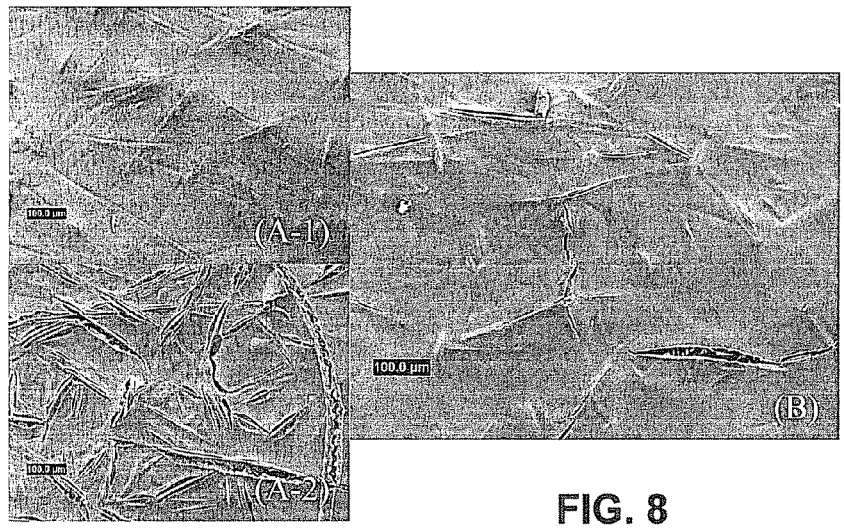

FIG. 8 depicts electron micrographic pictures (magnification: 100 μm) of polyester reinforced PNB from the smooth skin layer side. The membranes were coagulated at two different temperatures. (A-1) 20° C.; (A-2) 20° C.; (B) 60° C.

Figure 9:
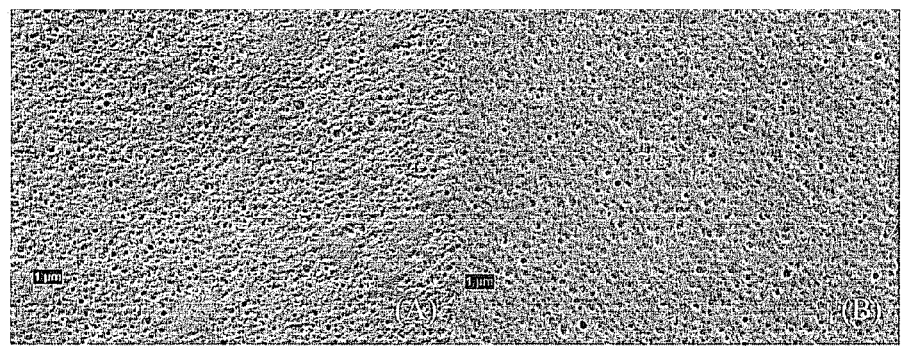
Figure 10:
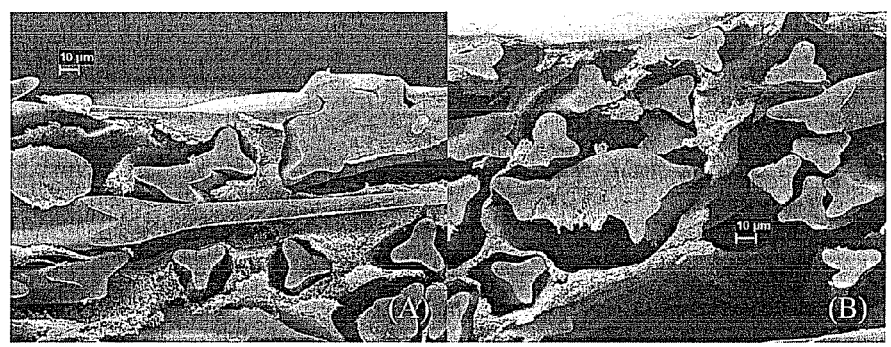

FIG. 9 depicts electron micrographic pictures (magnification: 1 μm) of polyester reinforced PNB from the smooth skin layer side. The membranes were coagulated at two different temperatures. (A) 20° C.; (B) 60° C.

FIG. 10 depicts electron micrographic pictures (magnification: 10 μm) of cross section of polyester reinforced PNB. The membranes were coagulated at two different temperatures. (A) 20° C.; (B) 60° C.

Operability Experiment of Single Thickness Films made from Different Polynorbornene Compositions A comparison of polynorbornene compositions was performed to observe performance of n-butanol in a pervaporation test. The two dependant variables that were examined were flux and separation factor. The feed solution concentration was fixed (about 5%). A heat bath was used to heat the feed solution to 65° C. Through heat loss, this gives a housing temperature of about 60° C. In order to collect the permeate samples vacuum traps in liquid nitrogen were used. The pressure of the vacuum was 20 in Hg. The feed solution was pumped into the system by a diaphragm pump at 70 mL/min. A three hour test was used to collect samples. A variety of terpolymer compositions were used as unsupported dense films. The typical thicknesses of the films were 30-50 microns and the effective diameter is 43.5 mm. The apparatus was designed with six housings that run simultaneously. The data for each test was an average of all of the housings. In the following Tables, SD stands for standard deviation. In all of the tables, the terpolymer composition is denoted by mole ratios of Monomer 1/Monomer 2/Monomer 3. NB stands for norbornene, HFANB stands for NB-hexafluoroisopropanol, GlycolNB stands for NB-$CH_2OCH_2CH_2OH$, PENB stands for NB-phenylethyl, HFIBONB stands for NB-methoxymethylhexafluoropropanol, HxNB stands for NB-hexyl, BuNB stands for NB-butyl.

| Membrane | 65/15/20 NB/DecylNB/HFANB | | 50/30/20 NB/DecylNB/HFANB | | 65/15/20 NB/GlycolNB/HFANB | | 50/30/20 NB/GlycolNB/HFANB | |
|---|---|---|---|---|---|---|---|---|
| | Average | SD | Average | SD | Average | SD | Average | SD |
| % BuOH | 30.22% | 4.66% | 55.31% | 6.65% | 40.51% | 7.26% | 20.93% | 0.80% |
| Selectivity | 8.34 | 1.81 | 23.99 | 6.4 | 13.24 | 3.68 | 5.03 | 0.24 |
| Flux | 112.53 | 9.15 | 284.72 | 106.72 | 411.71 | 82.38 | 474.36 | 79.92 |

| Membrane | 65/15/20 NB/PENB/HFANB | | 50/30/20 NB/PENB/HFANB | | 65/15/20 NB/PENB/HFIBONB | | 50/30/20 NB/PENB/HFIBONB | |
|---|---|---|---|---|---|---|---|---|
| | Average | SD | Average | SD | Average | SD | Average | SD |
| % BuOH | 36.93% | 0.76% | 19.67% | 9.01% | 26.08% | 2.15% | 25.59% | 4.08% |
| Selectivity | 11.13 | 0.36 | 4.92 | 2.71 | 6.72 | 0.74 | 6.59 | 1.42 |
| Flux | 311.02 | 49.96 | 400.29 | 141.02 | 124.91 | 41.98 | 156.31 | 0.81 |

| Membrane | 33/33/33 NB/PENB/HFANB | | 50/33/17 NB/PENB/HFANB | | 67/17/17 NB/PENB/HFANB | |
|---|---|---|---|---|---|---|
| | Average | SD | Average | SD | Average | SD |
| Thickness | 36.67 | 5.77 | 40.00 | 0.00 | 50.00 | 0.00 |
| % BuOH | 61.21% | 4.34% | 38.75% | 8.33% | 40.71% | 12.20% |
| Selectivity | 29.78 | 5.48 | 12.44 | 3.98 | 13.40 | 5.86 |
| Flux | 285.05 | 40.44 | 175.65 | 4.23 | 168.37 | 12.90 |

| Membrane | 55/20/25 NB/PENB/HFANB | | 67/8/25 NB/PENB/HFANB | | 8/8/38 NB/PENB/HFANB | |
|---|---|---|---|---|---|---|
| | Average | SD | Average | SD | Average | SD |
| Thickness | 30.00 | 0.00 | 40.00 | 0.00 | 46.67 | 5.77 |
| % BuOH | 50.71% | 9.67% | 47.28% | 12.03% | 56.16% | 11.81% |
| Selectivity | 20.92 | 7.18 | 16.39 | 7.50 | 23.46 | 9.45 |
| Flux | 201.85 | 27.63 | 372.51 | 32.72 | 462.34 | 4.87 |

| Membrane | 65/15/20 NB/HxNB/HFANB | | 50/30/20 NB/HxNB/HFANB | | 65/15/20 NB/BuNB/HFANB | | 50/30/20 NB/BuNB/HFANB | |
|---|---|---|---|---|---|---|---|---|
| | Average | SD | Average | SD | Average | SD | Average | SD |
| % BuOH | 27.70 | 13. | 34.14 | 15.81 | 29.44 | 9.10 | 5.34 | 9.96 |
| Selectivity | 7.42 | 4.9 | 9.66 | 5.46 | 9.33 | 3.83 | 1.24 | 2.45 |
| Flux | 157.00 | 82. | 156.48 | 63.54 | 274.65 | 86.21 | 113.70 | 52.43 |

| Membrane | 65/15/20 NB/HxNB/HFANB | | 50/30/20 NB/HxNB/HFANB | | 50/30/20 NB/BuNB/HFANB | |
|---|---|---|---|---|---|---|
| | Average | SD | Average | SD | Average | SD |
| % BuOH | 39.36 | 1.7 | 22.17 | 10.95 | 28.65 | 17.56 |
| Selectivity | 10.63 | 0.7 | 5.17 | 3.17 | 8.78 | 7.67 |
| Flux | 236.04 | 98. | 222.91 | 92.01 | 151.13 | 102.88 |

Experiment: Measuring SF and Flux for Various Butanol Concentrations

SF and flux were measured for various butanol concentrations in water using a 6 housing test apparatus at 60° C. with a membrane made of sample E NB/PENB/HFANB terpolymer having a Mw of 400,000-500,000. The results are reported in FIGS. 11, 12 and 13.

The feed was heated to 65° C. and charged at 70 mL/min while applying a vacuum of 20 in Hg to the apparatus. Membrane film thickness ranged from 30 to 40 microns.

Figure 11:
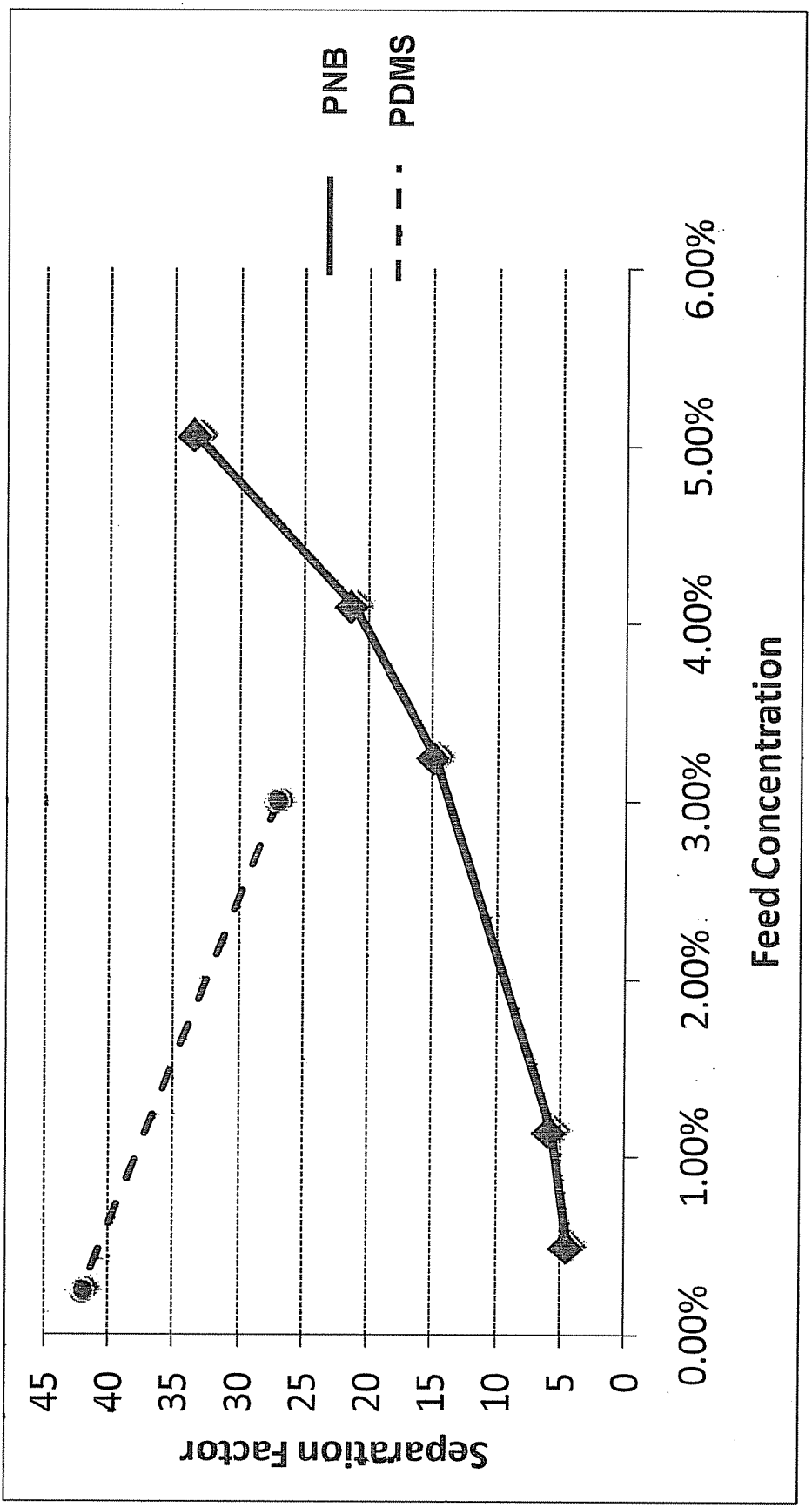
FIGS. 11 to 20 report the relationship amongst separation factor (SF), flux, and concentrations of butanol in accordance with various aspects of the invention.

FIG. 11 reports the increased SF achieved with increased concentrations of butanol, an unexpected result, as shown by the curve with a positive slope. An expected result is shown in FIG. 11 which reports the SF versus butanol concentration for a membrane made of polydimethylsiloxane (PDMS), a conventional pervaporation membrane, having a negative slope curve.

Figure 12:
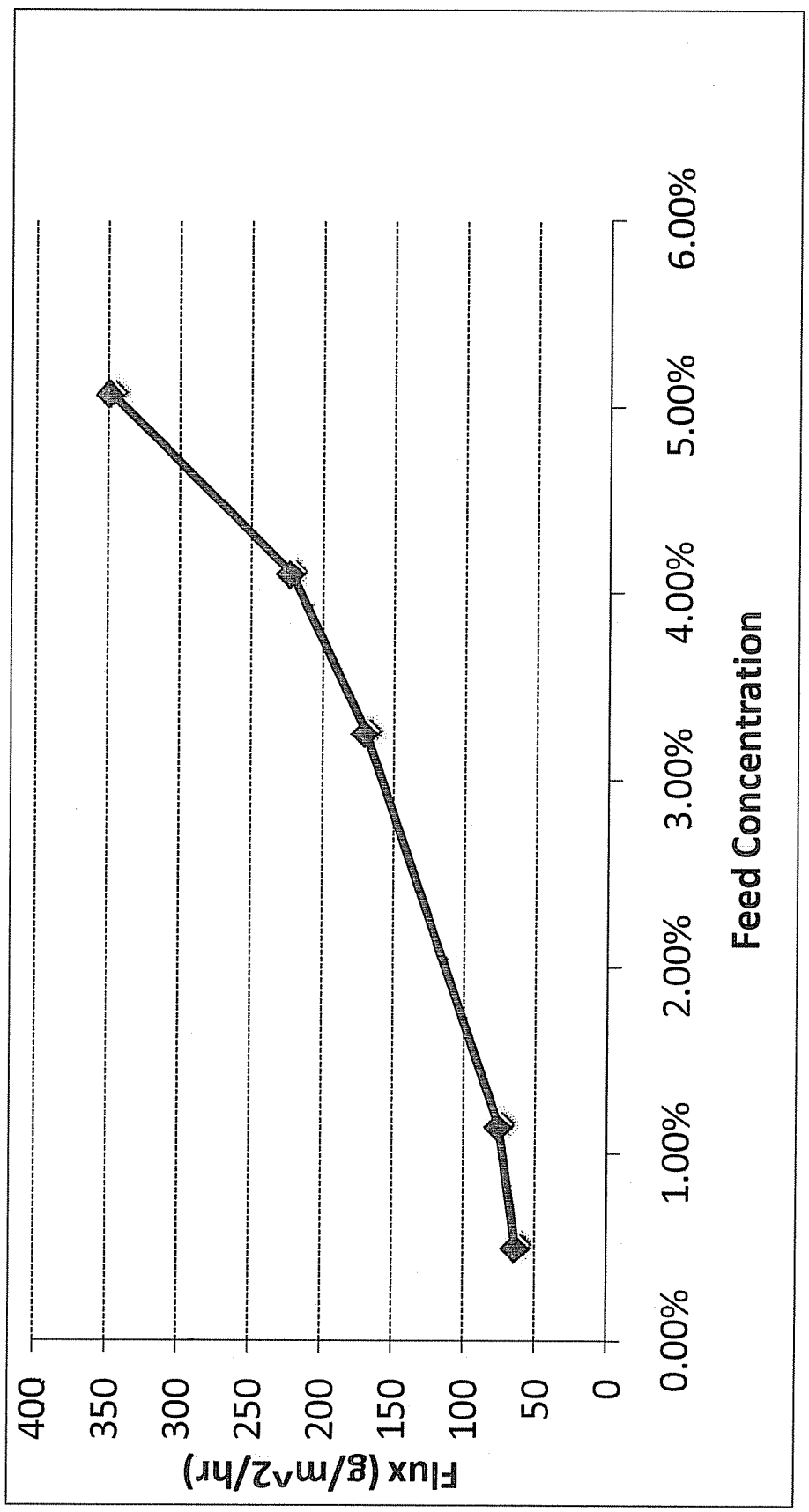

FIG. 12 reports the increased flux achieved with increased concentrations of butanol, another unexpected result, as shown by the curve with a positive slope.

Figure 13:
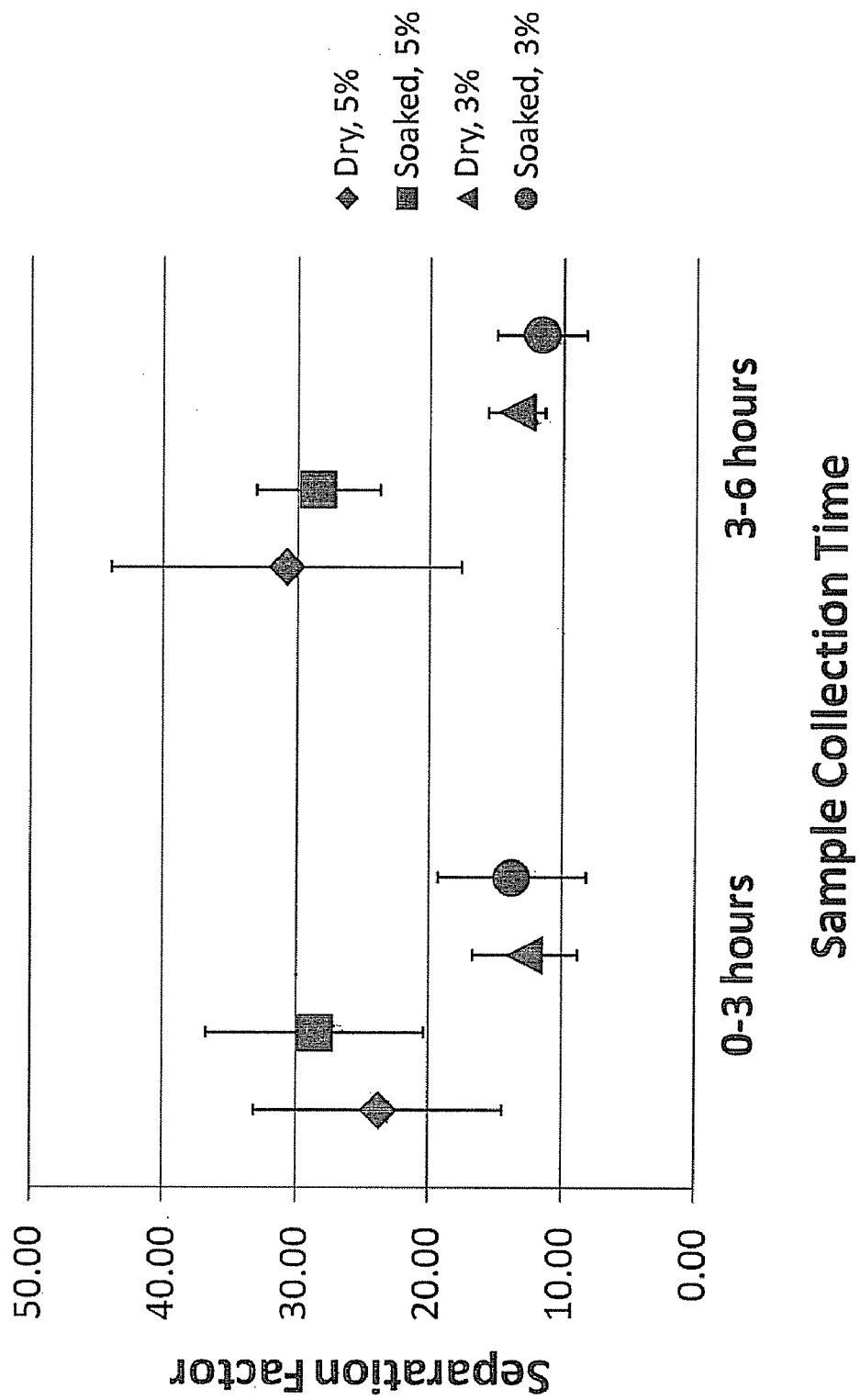

FIG. 13 demonstrates that SF is independent of the time duration of a pervaporation process as well as independent of whether or not the membrane is presoaked.

Operability Experiment of Single Thickness Films for Different Butanols

A comparison of alcohols was performed to observe performance of isobutanol and n-butanol in a pervaporation test. The two dependant variables that were examined were flux and separation factor. Varying concentrations of the feed solution (about 1%, 3%, and 5%) were used in each test to examine the affects of concentration. A heat bath was used to heat the feed solution to 65° C. Through heat loss, this gives a housing temperature of about 60° C. In order to collect the permeate samples vacuum traps in liquid nitrogen were used. The pressure of the vacuum was 20 in Hg. The feed solution was pumped into the system by a diaphragm pump at 70 mL/min. For feed concentrations of 3% or greater a three hour test was used to collect samples. Lower concentrations required more time to collect enough sample to analyze, and six hour tests were used in those cases. The same dense polymer film composition was used for all tests. The polymer film was a 33/33/33-NB/PENB/HFANB ter-polymer. These were used as unsupported dense films. The average thickness of the films is 40 microns and the effective diameter is 43.5 mm. The apparatus was designed with six housings that run simultaneously. The data for each test was an average of all of the housings. In the following Tables, Av stands for average while SD stands for standard deviation.

Isobutanol:

| | Feed Concentration, % | | | | | |
|---|---|---|---|---|---|---|
| | 1.15 | | 2.85 | | 5.47 | |
| | Av. | SD | Av. | SD | Av. | SD |
| Flux, g/($m^2 \cdot h$) | 51.1 | 9 | 94.6 | 15.8 | 173.3 | 24.6 |
| SF | 0.9 | 0.3 | 5.3 | 0.4 | 13.3 | 3.3 | n-Butanol:

| | Feed Concentration % | | | | | | | | | |
|---|---|---|---|---|---|---|---|---|---|---|
| | 0.48 | | 1.15 | | 3.25 | | 4.1 | | 5.06 | |
| | Av. | SD | Av. | SD | Av. | SD | Av. | SD | Av. | SD |
| Flux, g/($m^2 \cdot h$) | 63.4 | 16.5 | 75.8 | 16.1 | 170.1 | 23.9 | 222.0 | 46.6 | 348.1 | 80.5 |
| SF | 4.5 | 0.8 | 5.1 | 0.6 | 14.8 | 5.1 | 21.2 | 4.2 | 33.4 | 18.7 |

Examples of Forming of Thin Film Composites

Thin film composite (TFC) membranes were prepared in a similar fashion to the single thickness films. The difference is that a 5 micron polymer film is doctor bladed onto the Microdyn-Nadir 200K MWCO PVDF microfiltration membrane, which is secured to the glass panel. The PVDF sample that was coated is wider than the doctor blade to ensure an even coat. This was then allowed to air dry overnight. There is no soaking needed to lift the TFC off of the glass panel since the polymer remained on the surface of the PVDF.

| | Feed Concentration, % | | | | | |
|---|---|---|---|---|---|---|
| | 1.06 | | 3.01 | | 4.8 | |
| | Av. | SD | Av. | SD | Av. | SD |
| Flux, g/($m^2 \cdot h$) | 322.2 | 56.1 | 655 | 73.1 | 1098.8 | 127.9 |
| SF | 4.7 | 0.5 | 16.7 | 7.3 | 42.9 | 9.4 |

Figure 14:
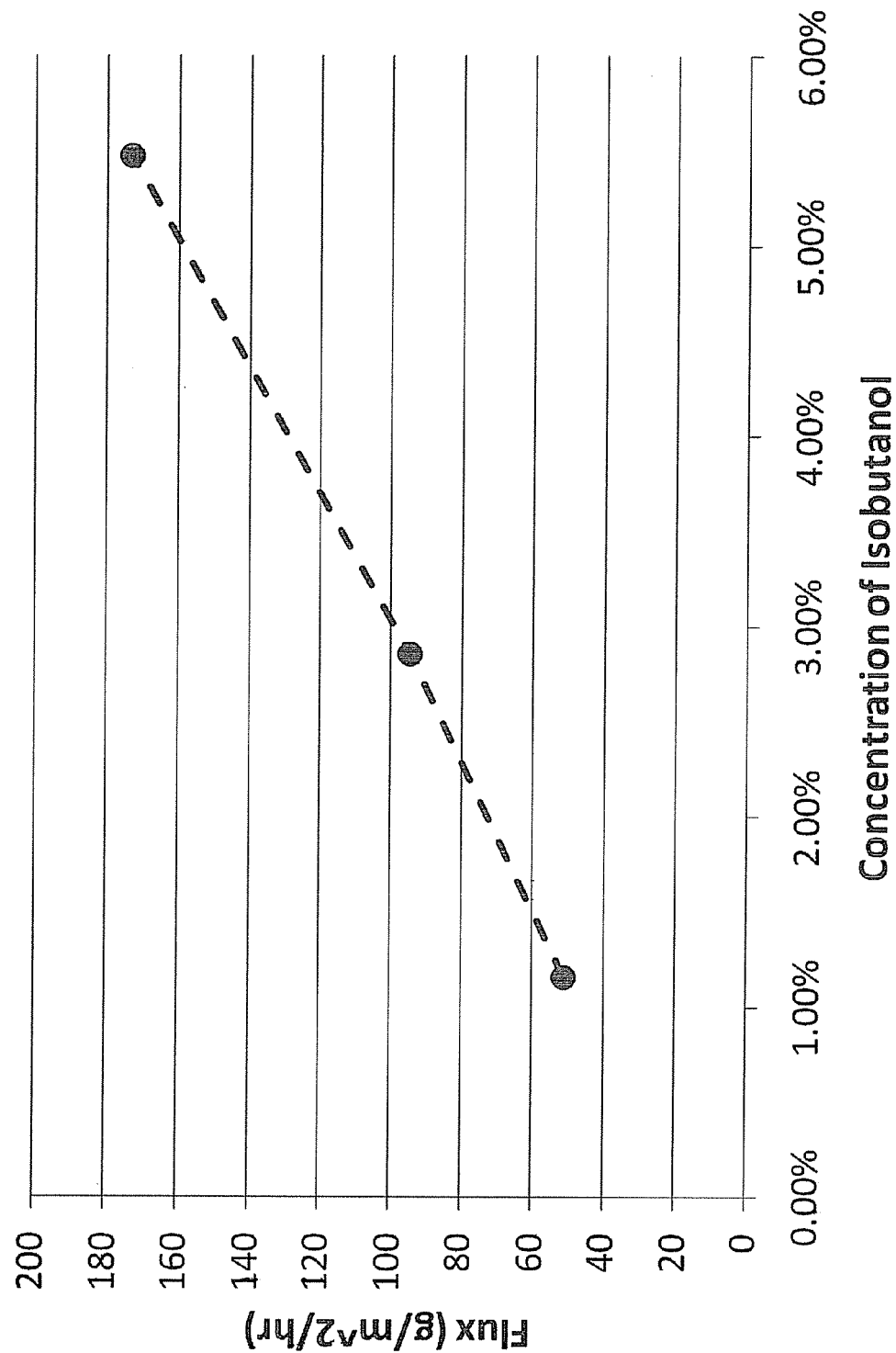
Figure 15:
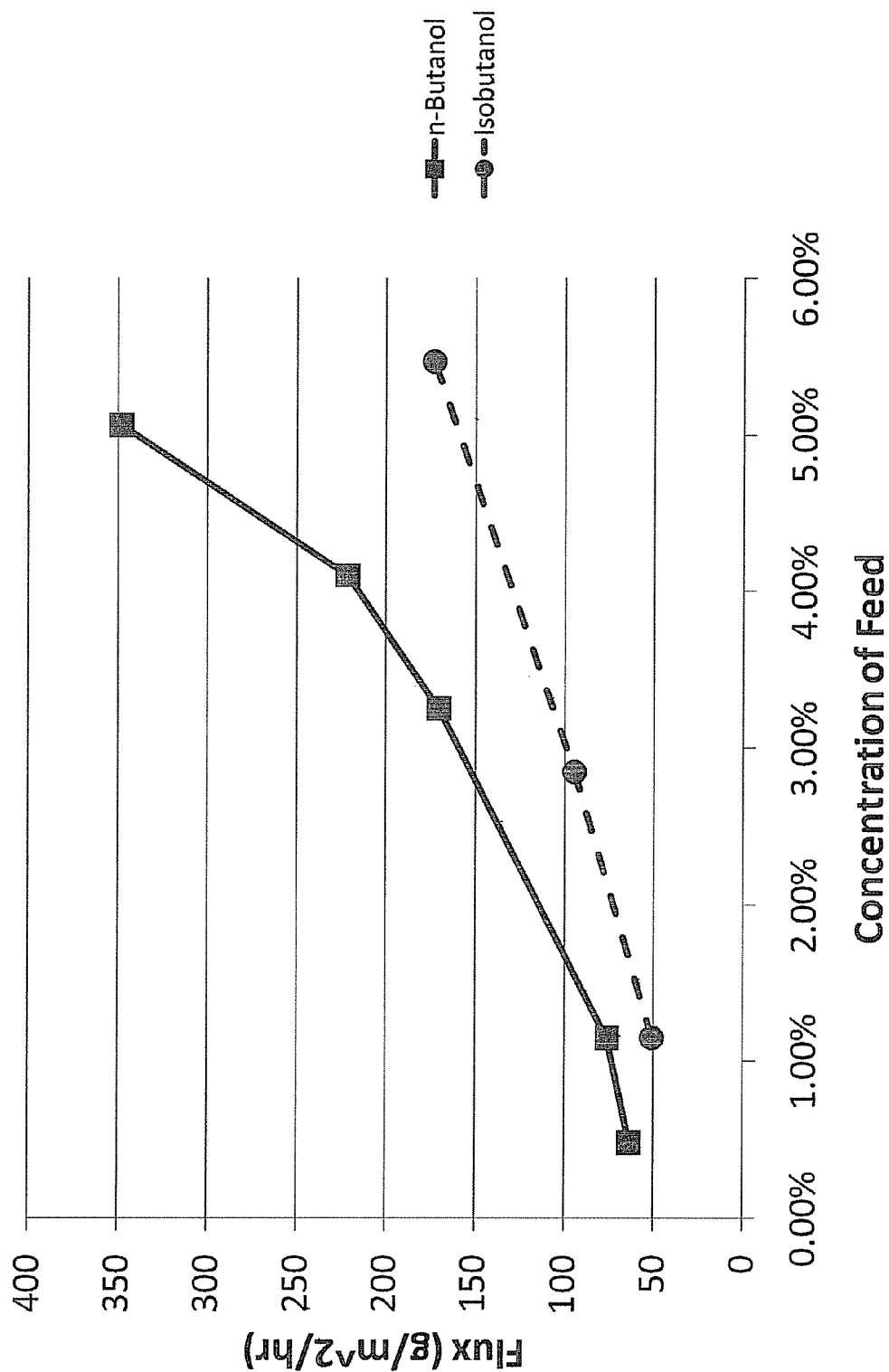
Figure 16:
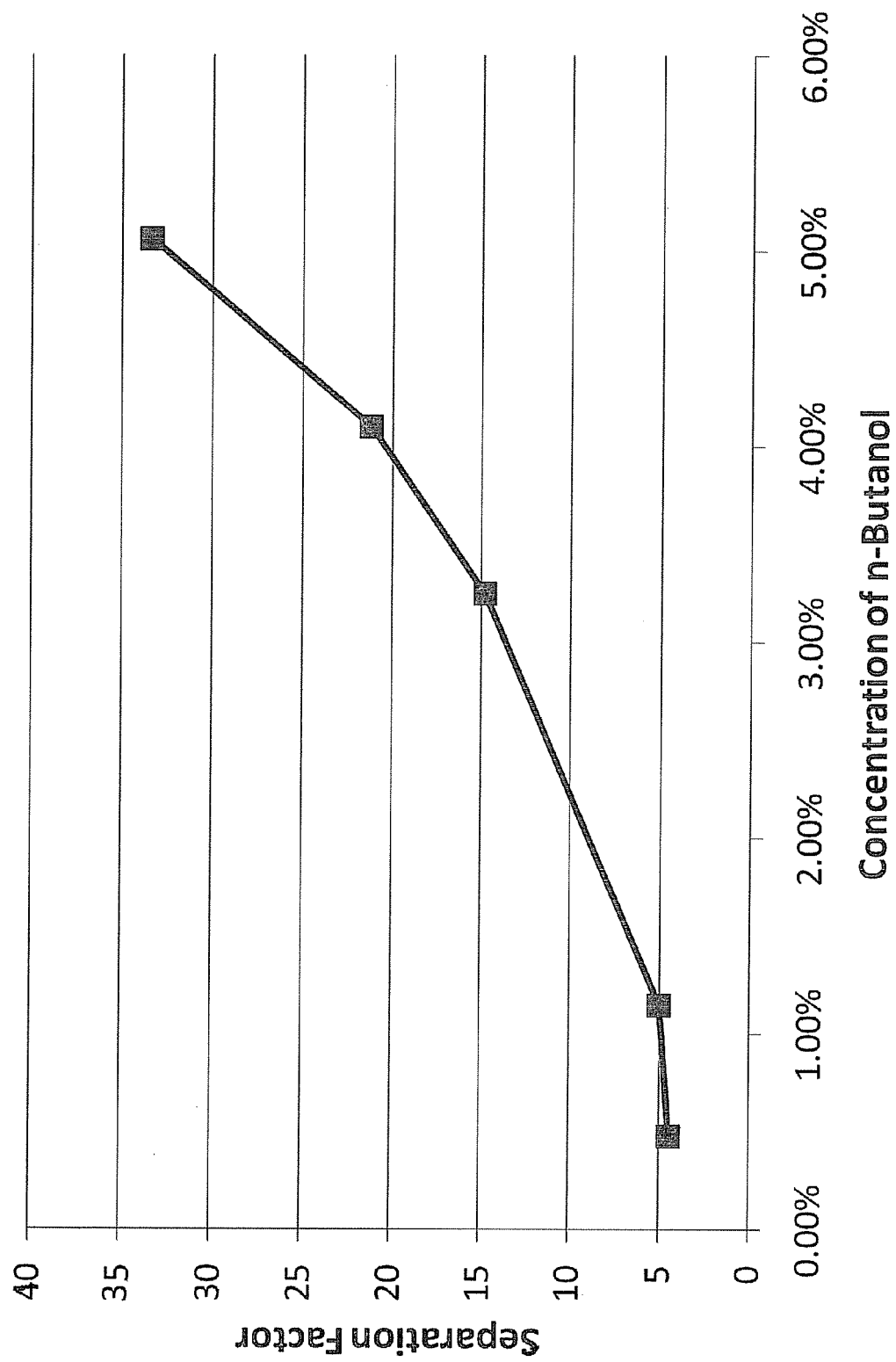
Figure 17:
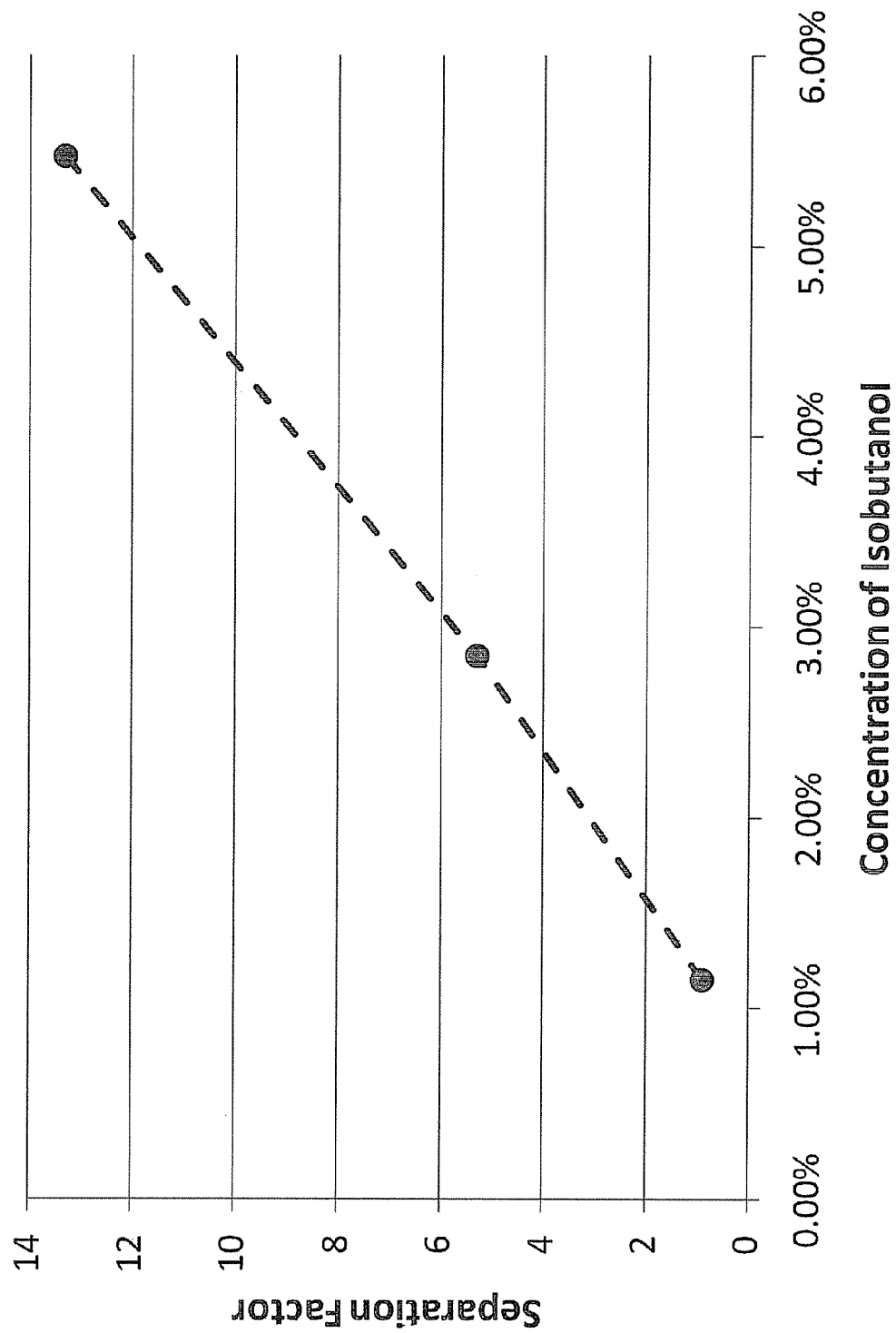
Figure 18:
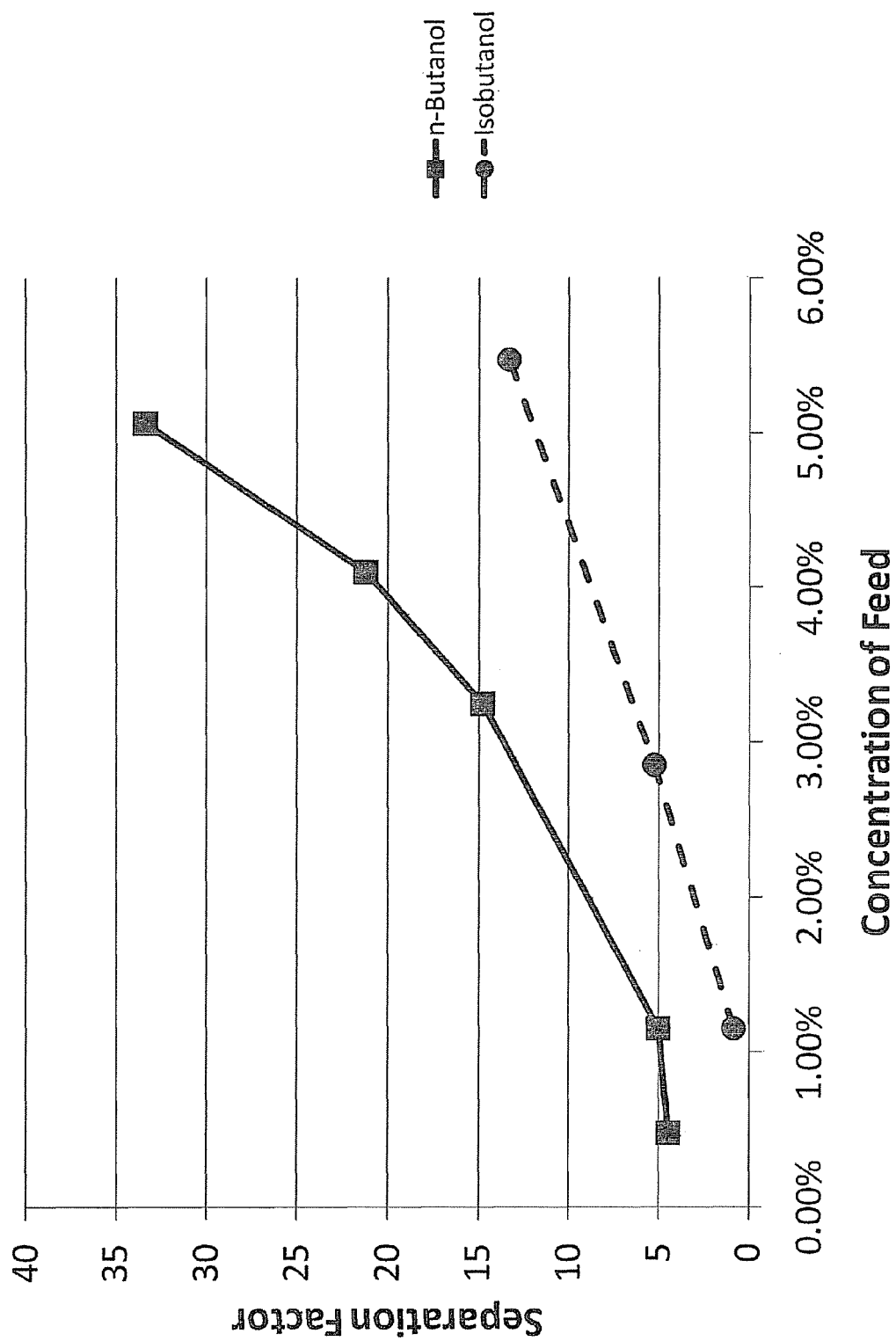
Figure 19:
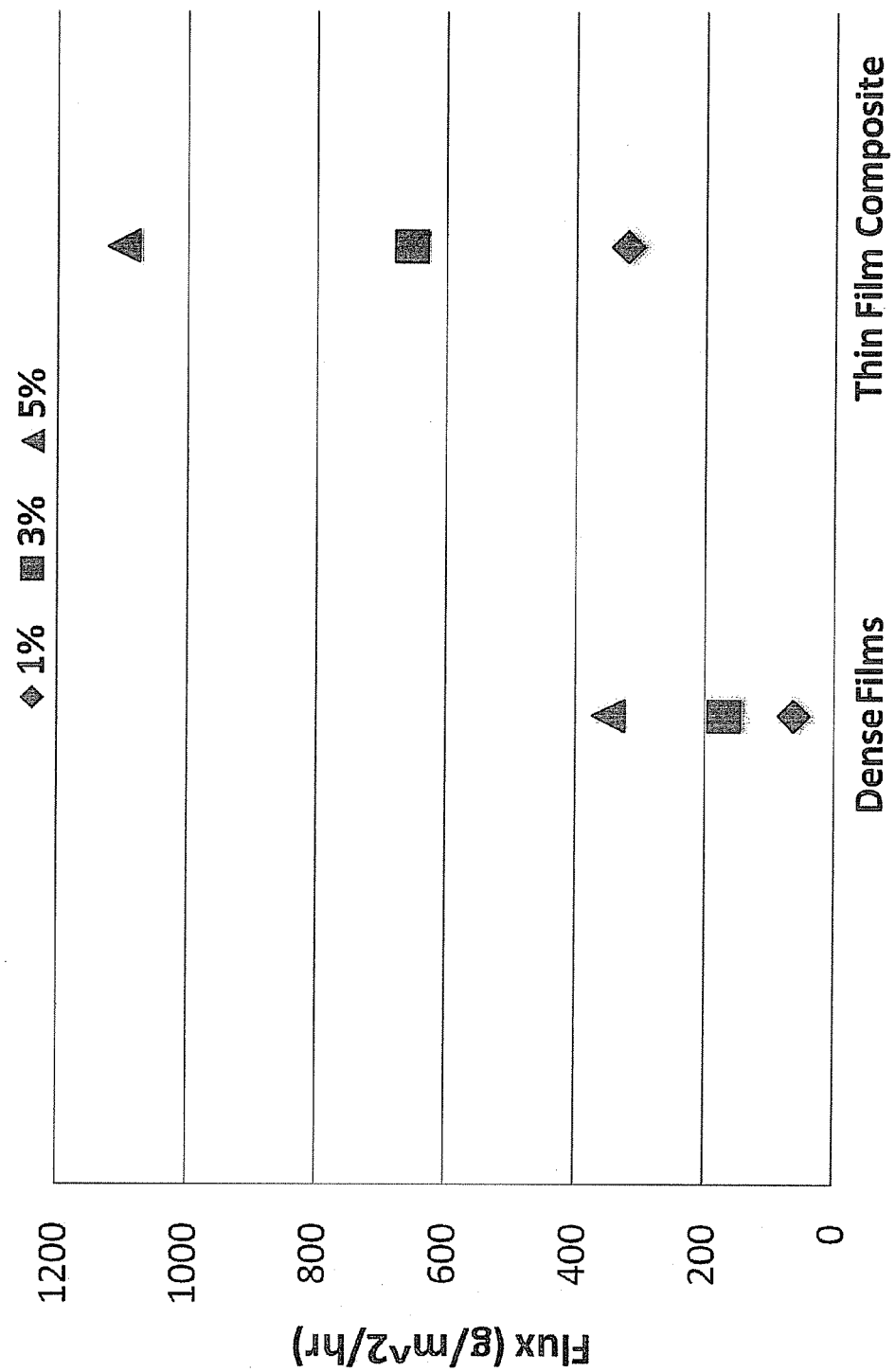
Figure 20:
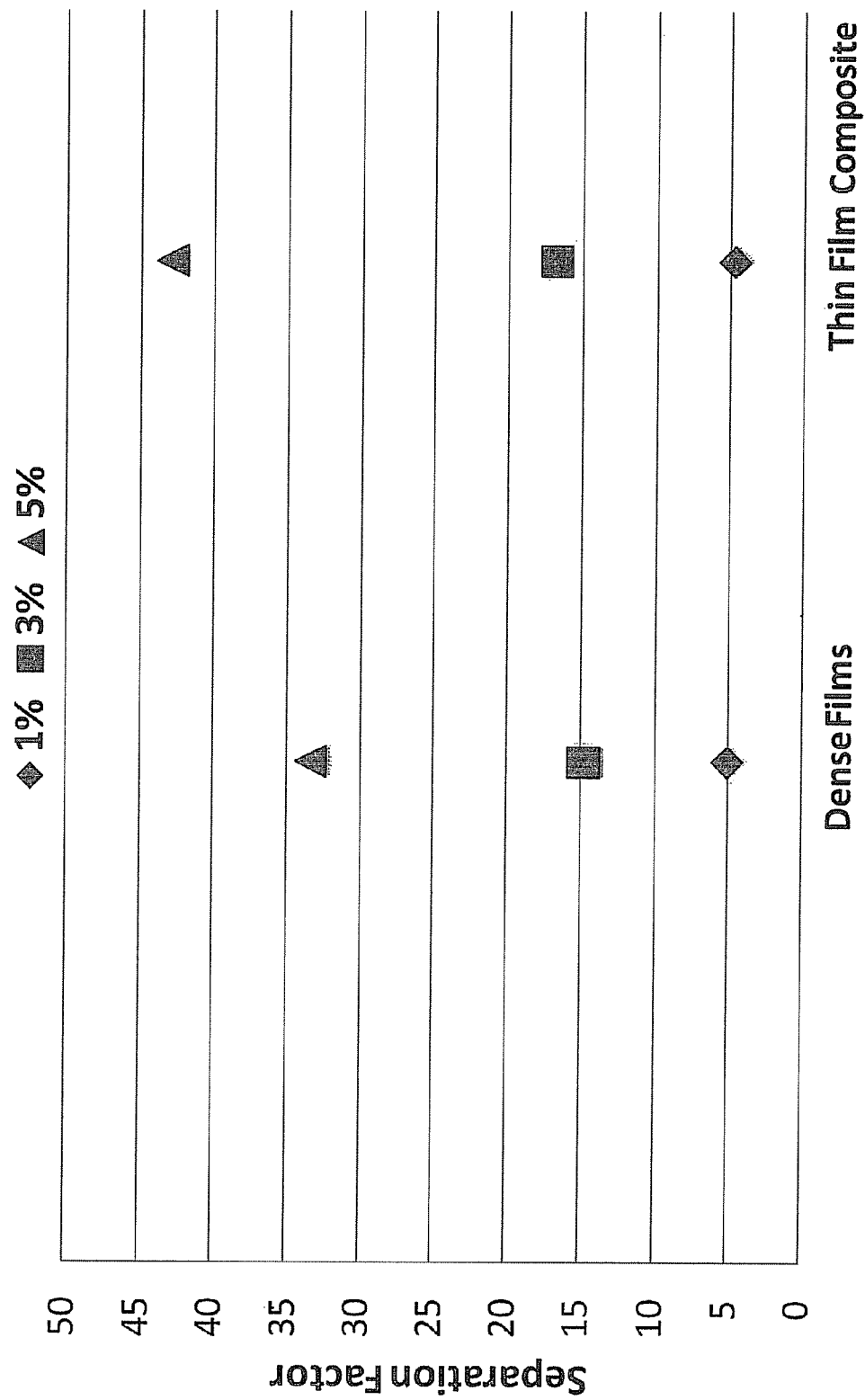

Various data from the above two sections are reported in the graphs in FIGS. 14 to 20. More specifically, FIG. 12 reports the increased flux achieved with increased concentrations of n-butanol. FIG. 14 reports the increased flux achieved with increased concentrations of isobutanol. FIG. 15 compares the flux achieved with increased concentrations of n-butanol and isobutanol. FIG. 16 reports the increased SF achieved with increased concentrations of n-butanol. FIG. 17 reports the increased SF achieved with increased concentrations of isobutanol. FIG. 18 compares the SF achieved with increased concentrations of n-butanol and isobutanol. FIG. 19 compares flux achieved with increased concentrations of n-butanol with a dense polymer film or TFC. FIG. 20 compares SF achieved with increased concentrations of n-butanol with a dense polymer film or TFC.

Finally it should be noted that while the evaluations of the polynorbornene materials presented herein focus on butanol laced charge liquids, it is anticipated that polynorbornene materials will be found to be selective to other organic materials found in other aqueous charge liquids or fermentation broths, or selective to non-polar materials in polar organic materials.

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A pervaporation membrane, comprising:
   a vinyl addition polynorbornene polymer having a Mw of at least about 5,000, the vinyl addition polynorbornene polymer comprising at least two different repeat units, wherein one of the repeat units, has a fluorinated carbinol moiety pendant group, the pervaporation membrane comprising a preferential permeability to a volatile organic over water, such permeability increasing with increasing organic concentration of a feed stream.

2. The pervaporation membrane according to claim 1 in a form of a tubular hollow fiber, a dense film flat sheet, or a thin film composite.

3. The pervaporation membrane according to claim 1, wherein the vinyl addition polynorbornene polymer comprises at least three different repeat units.

4. A pervaporation membrane, comprising:
   a polynorbornene polymer having a Mw of at least about 5,000, the vinyl addition polynorbornene polymer comprising at least two different repeat units, wherein one of the repeat units has a fluorinated carbinol moiety pendant group.

5. The pervaporation membrane according to claim 4 in a form of a tubular hollow fiber, a dense film flat sheet, or a thin film composite.

6. The pervaporation membrane according to claim 4 the pervaporation membrane comprising a preferential permeability to a volatile organic over water, such permeability increasing with increasing organic concentration of a feed stream.

7. The pervaporation membrane according to claim 4, wherein the polynorbornene polymer comprises at least three different repeat units.

8. The pervaporation membrane according to claim 6, wherein the volatile organic comprises butanol.

9. The pervaporation membrane according to claim 6 having a flux for butanol of at least about $100g/(m^2 \cdot h)$ from a fermentation broth comprising at least 1% by weight butanol, wherein the flux for butanol is an amount of butanol (q) that flows through a unit area ($m^2$) of the pervaporation membrane per unit of time (h).

10. The pervaporation membrane according to claim 4, comprising a co-polymer of HFANB and $C_1$-$C_{10}$ alkylNB.

11. A method of separating an organic product from a fermentation broth comprising the organic product, comprising:
charging the fermentation broth to a pervaporation module comprising a vinyl addition polynorbornene pervaporation membrane, the vinyl addition polynorbornene pervaporation membrane comprising a polynorbornene polymer having a Mw of at least about 5,000, the vinyl addition polynorbornene polymer comprising at least two different repeat units, wherein one of the repeat units has a fluorinated carbinol moiety pendant group; and
collecting a permeate vapor comprising the organic product from the pervaporation module.

12. The method according to claim 11, wherein the fermentation broth charged to the pervaporation module has a temperature from about 30° C. to about 90° C.

13. The method according to claim 11, wherein a vacuum from about 1 inHg to about 25 inHg is applied to the pervaporation module.

14. The method according to claim 11, wherein the vinyl addition polynorbornene pervaporation membrane comprises at least three different repeat units.

15. A method of separating butanol from a fermentation broth comprising butanol, comprising:
charging the fermentation broth to a pervaporation module comprising a polynorbornene pervaporation membrane, the vinyl addition polynorbornene pervaporation membrane comprising a polynorbornene polymer having a Mw of at least about 5,000, the vinyl addition polynorbornene polymer comprising at least two different repeat units, wherein one of the repeat units has a fluorinated carbinol moiety pendant group; and
collecting a permeate vapor comprising butanol from the pervaporation module.

16. The method according to claim 15, wherein the fermentation broth charged to the pervaporation module has a temperature from about 30° C. to about 90° C.

17. The method according to claim 15, wherein a vacuum from about 1 inHg to about 25 inHg is applied to the pervaporation module.

18. The method according to claim 15, wherein the polynorbornene pervaporation membrane comprises at least four different repeat units.

19. The method according to claim 15, wherein the polynorbornene pervaporation membrane comprises at least three different repeat units.

20. The method according to claim 15, wherein the polynorbornene pervaporation membrane comprises hydroxyhexafluoroisopropyl norbornene repeat units.

21. The method according to claim 15, wherein the polynorbornene pervaporation membrane has a separation factor of at least about 15 for butanol from a fermentation broth comprising at least 1% by weight butanol.

22. The method according to claim 15, wherein the polynorbornene pervaporation membrane has a flux of at least about 100 $g/(m^2 \cdot h)$ for butanol from a fermentation broth comprising at least 1% by weight butanol.

23. The method according to claim 15, wherein the polynorbornene pervaporation membrane comprises a polynorbornene polymer over a non-polynorbornene filtering component.

24. The method according to claim 15, wherein the polynorbornene pervaporation membrane comprises hydroxyhexafluoroisopropyl norbornene repeat units and $C_1$-$C_{10}$ alkyl norbornene repeat units.

25. The method according to claim 15, wherein the polynorbornene pervaporation membrane has a thickness from about 0.1 micron to about 500 microns.

26. The method according to claim 15, wherein the pervaporation feed stream comprise a biobutanol fermentation broth.

* * * * *